US008357488B2

(12) United States Patent
McGee et al.

(10) Patent No.: US 8,357,488 B2
(45) Date of Patent: Jan. 22, 2013

(54) **PRIMERS AND PROBES FOR THE DETECTION OF *STREPTOCOCCUS PNEUMONIAE***

(75) Inventors: Lesley McGee, Tucker, GA (US); Maria Lucia Tondella, Decatur, GA (US); Maria da Gloria Siqueira Carvalho, Atlanta, GA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 234 days.

(21) Appl. No.: 12/600,568

(22) PCT Filed: May 16, 2008

(86) PCT No.: PCT/US2008/063954
§ 371 (c)(1),
(2), (4) Date: Apr. 1, 2010

(87) PCT Pub. No.: WO2009/011971
PCT Pub. Date: Jan. 22, 2009

(65) Prior Publication Data
US 2010/0234245 A1    Sep. 16, 2010

Related U.S. Application Data

(60) Provisional application No. 60/938,799, filed on May 18, 2007.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ....... 435/6.1; 435/91.2; 536/23.1; 536/24.3

(58) Field of Classification Search .................... None
See application file for complete search history.

(56) References Cited

U.S. PATENT DOCUMENTS 6,800,744 B1 * 10/2004 Doucette-Stamm et al. 536/23.1
2011/0177960 A1 * 7/2011 Murphy et al. ............. 506/9

FOREIGN PATENT DOCUMENTS

EP         1770171       4/2007
WO    WO 2006/104486   10/2006

OTHER PUBLICATIONS

Buck, G.A. et al., Biotechniques, vol. 27, pp. 528-536 (1999).*
Arbique et al., "Accuracy of Phenotypic and Genotypic Testing for Identification of *Streptococcus pneumoniae* and Description of *Streptococcus pseudopneumoniae* sp. nov.", *Journal of Clinical Microbiology*, vol. 42, No. 10, pp. 4686-4696, 2004.
Carvalho et al., "Evaluation and Improvement of Real-Time PCR Assays Targeting *lytA*, *ply*, and *psaA* Genes for Detection of Pneumococcal DNA", *Journal of Clinical Microbiology*, vol. 45, No. 8, pp. 2460-2466, 2007.
Carvalho et al., "Development and Evaluation of Real-Time PCR Detection Assays to *psa,A lytA*, and *ply*, Genes for Diagnosis of Pneumococcal Disease", *ASM 105th General Meeting*, vol. 105, pp. 132-133, C-144, 2005, Abstract.
Corless et al., "Simultaneous Detection of *Neisseria meningitides*, *Haemophilus influenza*, and *Streptococcus pneumoniae* in Suspected Cases of Meningitis and Septicemia Using Real-Time PCR", *Journal of Clinical Microbiology*, vol. 39, No. 4, pp. 1553-1558, 2001.
Gillespie et al., "Detection of *Streptococcus pneumoniae* in Sputum Samples by PCR", *Journal of Clinical Microbiology*, vol. 32, No. 5, pp. 1308-1311, 1994.
Kaijalainen, "Identification of *Streptococcus pneumoniae*", *International Journal of Circumpolar Health*, vol. 65, No. 5, pp. 459-460, 2006, Abstract.
Li et al., "Rapid, Sensitive and Quantitative Detection of *Streptococcus pneumoniae* Using Triplex Real-Time PCR", *ASM 105th General Meeting*, vol. 105, pp. 132, C-143, 2005, Abstract.
Llull et al., "Characteristic Signatures of the *lytA* Gene Provide a Basis for Rapid and Reliable Diagnosis of *Streptococcus pneumoniae* Infections", *Journal of Clinical Microbiology*, vol. 44, No. 4, pp. 1250-1256, 2006.
McAvin et al., "Sensitive and Specific Method for Rapid Identification of *Streptococcus pneumoniae* Using Real-Time Fluorescence PCR", *Journal of Clinical Microbiology*, vol. 39, No. 10, pp. 3446-3451, 2001.
Messmer et al., "Comparison of four polymerase chain reaction assays for specificity in the identification of *Streptococcus pneumoniae*", *Diagnostic Microbiology and Infectious Disease*, vol. 49, pp. 249-254, 2004.
Messmer et al., "Use of polymerase chain reaction to identify pneumococcal infection associated with hemorrhage and shock in two previously healthy young children", *Clinical Chemistry*, vol. 43, No. 6, pp. 930-935, 1997.
Morozumi et al., "Simultaneous Detection of Pathogens in Clinical Samples from Patients with Community-Acquired Pneumonia by Real-Time PCR with Pathogen-Specific Molecular Beacon Probes", *Journal of Clinical Microbiology*, vol. 44, No. 4, pp. 1440-1446, 2006.
Nagai et al., "Evaluation of PCR primers to screen for *Streptococcus pneumoniae* isolates and β-lactam resistance, and to detect common macrolide resistance determinants", *Journal of Antimicrobial Chemotherapy*, vol. 48, pp. 915-918, 2001.

(Continued)

*Primary Examiner* — Teresa E Strzelecka
(74) *Attorney, Agent, or Firm* — Klarquist Sparkman, LLP.

(57) ABSTRACT

Methods of detecting *Streptococcus pneumoniae* (*S. pneumoniae*), are disclosed. A sample suspected of containing a nucleic acid of *S. pneumoniae* is screened for the presence or absence of that nucleic acid. The presence of the *S. pneumoniae* nucleic acid indicates the presence of *S. pneumoniae*. Determining whether the *S. pneumoniae* nucleic acid is present in the sample can be accomplished by detecting hybridization between a *S. pneumoniae* probe, such as a *S. pneumoniae* lytA probe, a *S. pneumoniae* psaA probe, or a *S. pneumoniae* ply probe. Probes and primers for the detection of *S. pneumoniae* are also disclosed. Kits and arrays that contain the disclosed probes and/or primers also are disclosed.

14 Claims, 5 Drawing Sheets

OTHER PUBLICATIONS

Rubin and Rizvi, "PCR-based assays for detection of *Streptococcus pneumoniae* serotypes 3, 14, 19F and 23F in respiratory specimens", *Journal of Medical Microbiology*, vol. 53, pp. 595-602, 2004.

Seki et al., "Loop-Mediated Isothermal Amplification Method Targeting the *lytA* Gene for Detection of *Streptococcus pneumoniae*", *Journal of Clinical Microbiology*, vol. 43, No. 4, pp. 1581-1586, 2005.

Sheppard et al., "Autolysin-targeted LightCycler assay including internal process control for detection of *Streptococcus pneumoniae* DNA in clinical samples", *Journal of Medical Microbiology*, vol. 53, pp. 189-195, 2004.

Suzuki et al., "Genotypic identification of presumptive *Streptococcus pneumoniae* by PCR using four genes highly specific for *S. pneumoniae*", *Journal of Medical Microbiology*, vol. 55, pp. 709-714, 2006.

Ubukata et al., "Combinational Detection of Autolysin and Penicillin-Binding Protein 2B Genes of *Streptococcus pneumoniae* by PCR", *Journal of Clinical Microbiology*, vol. 34, No. 3, pp. 592-596, 1996.

Verhelst et al., "Comparison of Five Genotypic Techniques for Identification of Optochin-Resistant Pneumococcus-Like Isolates", *Journal of Clinical Microbiology*, vol. 41, No. 8, pp. 3521-3525, 2003.

\* cited by examiner psaA-CDC; HEX, Y=-3.403*LOG(X)+42.42, Eff.= 96.7% lytA-CDC; FAM2, Y=-3.3.363*LOG(X)+41.12, Eff. = 98.3% lytA-McAvin FAM, Y=-3.292*LOG(X)+41.37, Eff. = 101.3% ply-CDC; FAM2, Y=-3.400*LOG(X)+40.56, Eff. =96.8% ply-Corless, FAM3, Y=-3.310*LOG(X)+40.75, Eff. = 100.5%

PRIMERS AND PROBES FOR THE DETECTION OF *STREPTOCOCCUS PNEUMONIAE*

CROSS REFERENCE TO RELATED APPLICATIONS

This is the §371 U.S. National Stage of International Application No. PCT/US2008/063954, filed May 16, 2008, which was published in English under PCT Article 21(2), which in turn claims the benefit of U.S. Provisional Application No. 60/938,799 filed May 18, 2007, which is incorporated by reference herein in its entirety.

FIELD

This disclosure relates to primers and probes for detecting *Streptococcus pneumoniae*, as well as kits including the probes and primers and methods of using the probes and primers.

BACKGROUND

*Streptococcus pneumoniae* (*S. pneumoniae*) is a Gram-positive bacteria responsible for considerable morbidity and mortality (particularly in the young and aged), causing diseases such as pneumonia, bacteremia, meningitis, acute otitis media, and sinusitis. It is estimated the 20% of *S. pneumoniae* cases lead to bacteremia, and other manifestations such as meningitis, with a mortality rate close to 30% even with antibiotic treatment. *S. pneumoniae* is found in the nasopharynx of 11-76% of the population, averaging 40-50% for children and 20-30% for adults (Ghaffar et al., *J. Infect. Dis.* 18, 638-46, 1999).

Those most commonly at risk for pneumococcal infection are children between 6 months and 4 years of age and adults over 60 years of age. Virtually every child will experience pneumococcal otitis media before the age of 5 years. It is estimated that 25% of all community-acquired pneumonia is due to pneumococcus (1,000 per 100,000 inhabitants). Recently, epidemics of disease have reappeared in settings such as chronic care facilities, military camps, and day care centers, a situation not recognized since the pre-antibiotic era. *S. pneumoniae* remains a significant human pathogen because of the morbidity and mortality it causes in young children, the elderly and in immunocompromised patients.

The limitations of culture based, conventional *S. pneumoniae* diagnostic tests make definitive diagnosis difficult to establish. For example, the isolation of *S. pneumoniae* from blood, the recognized definitive test for the presence of *S. pneumoniae* may lack sensitive, only giving positive results in 20-30% of adult cases of pneumococcal pneumonia and less than 10% of children's cases. Serologic assays for both antibody and antigen detection suffer from a lack of specificity and sensitivity, for example the recently introduced urine antigen test, Binax NOW®, while shown to be sensitive and specific for adults by some studies, is unable to distinguish between carriage and disease in children.

In addition, the misidentification of pneumococcus-like viridans Streptococci (P-LVS) as *S. pneumoniae* presents additional opportunities for misdiagnosis especially when attempted with non-sterile site specimens such as sputum. Identification of *S. pneumoniae* has typically been based on bile solubility, optochin sensitivity, and GenProbe ACCU-PROBE® Pneumococcus identification test; but increasingly there have been reports of P-LVS isolated from clinical specimens, which may give positive or variable reactions in one or more of these standard pneumococcal tests. Among a subset of reported isolates of P-LVS, a newly recognized species, classified as *S. pseudopneumoniae* (Spseudo), has been described and characterized (Arbique et al., *J. Clin. Microbiol.* 42: 4686-4696, 2004). Spseudo organisms are bile solubility negative and resistant to optochin in the presence of 5% $CO_2$, but are ACCUPROBE® positive (Arbique et al., *J. Clin. Microbiol.* 42: 4686-4696, 2004) and thus yield a false positive for *S. pneumoniae* infection.

The appearance of these pneumococcus-like organisms has complicated identification and diagnosis even further, especially when non-sterile site respiratory specimens are used for making determinations. Therefore, special care must be taken to monitor and correctly identify confirmed pneumococci in the clinical setting. Thus, to make an accurate diagnosis the need exists for assays that can discriminate between *S. pneumoniae* and the Spseudo and other P-LVS species. The present disclosure meets this need by providing assays that can discriminate between *S. pneumoniae* and other organisms while still retaining high sensitivity for *S. pneumoniae*.

SUMMARY

Accurate diagnosis of pneumococcal disease is frequently hampered by the misidentification of pneumococcus-like viridans streptococci species (P-LVS) as *Streptococcus pneumoniae* (*S. pneumoniae*). In order to achieve an accurate diagnosis, an assay should be both sensitive and highly specific for diagnosis of the disease, such as the diagnosis of a *S. pneumoniae* infection. By analyzing regions of the lytA, ply, and psaA genes that are unique *S. pneumoniae*, assays disclosed herein have been developed that are highly specific for *S. pneumoniae* while retaining high sensitivity for *S. pneumoniae*. Because the disclosed assays are both sensitive and specific, the presence of *S. pneumoniae* in non-sterile samples, such as samples obtained from a subject, can be reliably determined. Such accuracy is important for medical professionals to make the best possible diagnosis and treatment plan, particularly in the age of over-prescription of medication, such as antibiotics. In addition, because the assays are highly specific for nucleic acids from *S. pneumoniae* and do not show cross reaction with the nucleic acids from other organisms the assay is well suited to multiplexing, for example in a multiplex real-time PCR assay for detecting multiple pathogens that may be present in a sample, such as a sample obtained from a subject.

The present disclosure relates to methods of detecting the presence of *Streptococcus pneumoniae* (*S. pneumoniae*) nucleic acids in a sample, such as a biological sample obtained from a subject, for example to detect *S. pneumoniae* in the sample. The disclosed methods can be used for diagnosing an *S. pneumoniae* infection, for example in a subject suspected of having an *S. pneumoniae* infection, by analyzing a biological specimen from a subject to detect a broad variety of *S. pneumoniae* nucleic acids, such as *S. pneumoniae* lytA, ply, and psaA nucleic acids using the probes and/or primers disclosed herein. In addition, the probes and primers provided permit the rapid evaluation of a subject with an apparent *S. pneumoniae* infection by quickly determining whether the infection is caused by *S. pneumoniae* or another organism. This rapid evaluation involves ruling out the presence of *S. pneumoniae*, ruling in the presence of *S. pneumoniae*, or a combination of both, for example in a multiplex real-time PCR assay.

In some embodiments, the method involves hybridizing an *S. pneumoniae* nucleic acid to an *S. pneumoniae* specific probe between 20 and 40 nucleotides in length, and detecting hybridization between the S. pneumoniae nucleic acid and the probe. In some embodiments, the probe is detectably labeled. In some embodiments, the probe is capable of hybridizing under conditions of very high stringency to a S. pneumoniae nucleic acid sequence set forth as SEQ ID NO: 13 (the lytA gene from S. pneumoniae), SEQ ID NO: 14 (the psaA gene from S. pneumoniae), or SEQ ID NO: 15 (the ply gene from S. pneumoniae). In specific embodiments, the probe includes a nucleic acid sequence that is at least 95% identical to a nucleic acid sequence set forth as SEQ ID NO: 5, SEQ ID NO: 6, SEQ ID NO: 9, or SEQ ID NO: 12.

The present disclosure also relates to methods of detecting and/or discriminating between S. pneumoniae or another organism, such as a bacterial organism, for example pneumococcus-like viridans Streptococci (P-LVS), such as S. pseudopneumoniae (Spseudo).

In some embodiments, the methods disclosed herein include amplifying the S. pneumoniae nucleic acids with at least one primer specific for a S. pneumoniae nucleic acid. In some embodiments, the primer specific for a S. pneumoniae nucleic acid is 15 to 40 nucleotides in length and is capable of hybridizing under very high stringency conditions to a S. pneumoniae nucleic acid sequence set forth as SEQ ID NO: 13, SEQ ID NO: 14, or SEQ ID NO: 15. In some embodiments, the primer specific for a S. pneumoniae nucleic acid is 15 to 40 nucleotides in length and includes a nucleic acid sequence at least 95% identical to the nucleotide sequence set forth as SEQ ID NO: 3, SEQ ID NO: 4, SEQ ID NO: 7, SEQ ID NO: 8, SEQ ID NO: 10, or SEQ ID NO: 11.

In some embodiments, the S. pneumoniae nucleic acid is amplified using at least one primer, such as a pair of primers, specific for a S. pneumoniae gene, such as a S. pneumoniae lytA, psaA, or ply gene. In some examples, a primer specific for S. pneumoniae lytA includes a nucleic acid sequence at least 95% identical to the nucleic acid sequence set forth as one of SEQ ID NO: 3 or SEQ ID NO: 4. In other examples, a primer specific for S. pneumoniae psaA includes a nucleic acid sequence at least 95% identical to the nucleic acid sequence set forth as one of SEQ ID NO: 7 or SEQ ID NO: 8. In other examples, a primer specific for S. pneumoniae ply includes a nucleic acid sequence at least 95% identical to the nucleic acid sequence set forth as one of SEQ ID NO: 10 or SEQ ID NO: 11.

This disclosure also relates to probes capable of hybridizing to S. pneumoniae nucleic acids, such as S. pneumoniae lytA, psaA, or ply nucleic acids. In some embodiments, these probes are between 20 and 40 nucleotides in length and capable of hybridizing under very high stringency conditions to a S. pneumoniae nucleic acid sequence set forth as SEQ ID NO: 12, SEQ ID NO: 13, or SEQ ID NO: 14. In several examples, these probes are between 20 and 40 nucleotides in length and include a nucleic acid sequence set forth as SEQ ID NO: 5, SEQ ID NO: 6, SEQ ID NO: 9, or SEQ ID NO: 12.

This disclosure also relates to primers capable of hybridizing to and amplifying S. pneumoniae nucleic acids, such as S. pneumoniae lytA, psaA, or ply nucleic acids. In some embodiments, these primers are between 20 and 40 nucleotides in length and capable of hybridizing under very high stringency conditions to a S. pneumoniae nucleic acid sequence set forth as SEQ ID NO: 13, SEQ ID NO: 14, or SEQ ID NO: 15. In several examples, these primers are 15 to 40 nucleotides in length and include a nucleic acid sequence at least 95% identical to a nucleic acid sequence set forth as SEQ ID NO: 3, SEQ ID NO: 4, SEQ ID NO: 7, SEQ ID NO: 8, SEQ ID NO: 11, or SEQ ID NO: 12.

The disclosure also provides devices, such as arrays, as well as kits for detecting S. pneumoniae nucleic acids in a sample suspected of containing S. pneumoniae.

The foregoing and other objects, features, and advantages of the invention will become more apparent from the following detailed description, which proceeds with reference to the accompanying figures.

SEQUENCE LISTING

Figure 1:
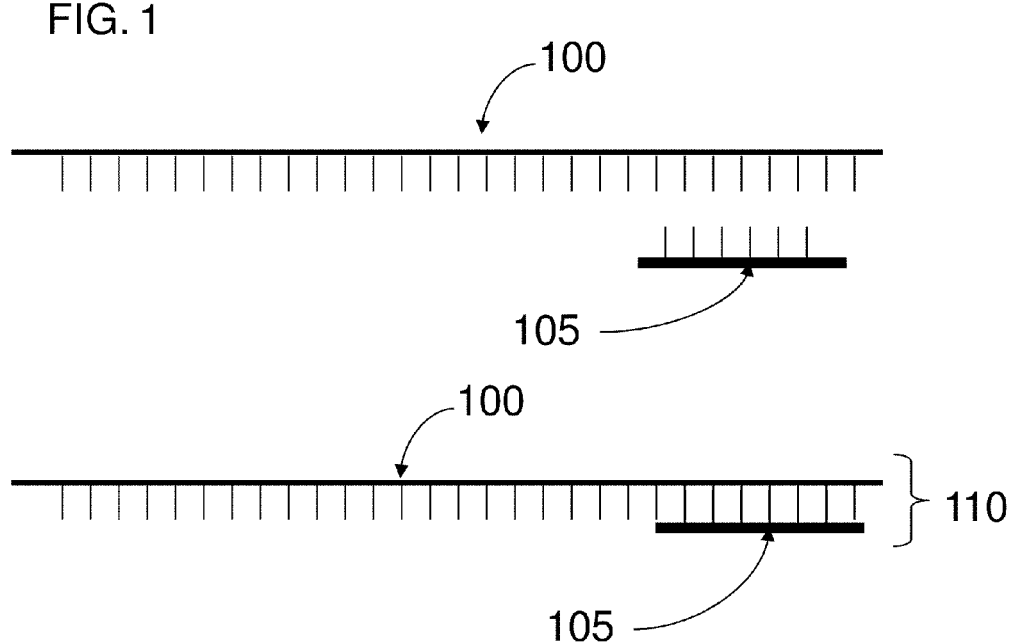
FIG. 1 is a schematic representation of a generalized procedure for hybridizing a S. pneumoniae specific probe to a S. pneumoniae nucleic acid.

The nucleic and amino acid sequences listed in the accompanying sequence listing are shown using standard letter abbreviations for nucleotide bases, and one letter code for amino acids, as defined in 37 C.F.R. §1.822. If only one strand of each nucleic acid sequence is shown, the complementary strand is understood as included by any reference to the displayed strand.

SEQ ID NO: 1 is the nucleotide sequence of a theoretical oligo.

SEQ ID NO: 2 is the nucleotide sequence of a theoretical oligo.

SEQ ID NO: 3 is the nucleotide sequence of a Streptococcus pneumoniae lytA forward real-time PCR primer.

SEQ ID NO: 4 is the nucleotide sequence of a Streptococcus pneumoniae lytA reverse real-time PCR primer.

SEQ ID NO: 5 is the nucleotide sequence of a Streptococcus pneumoniae lytA real-time PCR probe.

SEQ ID NO: 6 is the nucleotide sequence of a Streptococcus pneumoniae lytA real-time PCR probe.

SEQ ID NO: 7 is the nucleotide sequence of a Streptococcus pneumoniae psaA forward real-time PCR primer.

SEQ ID NO: 8 is the nucleotide sequence of a Streptococcus pneumoniae psaA reverse real-time PCR primer.

SEQ ID NO: 9 is the nucleotide sequence of a Streptococcus pneumoniae psaA real-time PCR probe.

SEQ ID NO: 10 is the nucleotide sequence of a Streptococcus pneumoniae ply forward real-time PCR primer.

SEQ ID NO: 11 is the nucleotide sequence of a Streptococcus pneumoniae ply reverse real-time PCR primer.

SEQ ID NO: 12 is the nucleotide sequence of a Streptococcus pneumoniae ply real-time PCR probe.

SEQ ID NO: 13 is an exemplary nucleotide sequence of Streptococcus pneumoniae lytA.

SEQ ID NO: 14 is an exemplary nucleotide sequence of Streptococcus pneumoniae psaA.

SEQ ID NO: 15 is an exemplary nucleotide sequence of Streptococcus pneumoniae ply.

DETAILED DESCRIPTION

I. Explanation of Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "a probe" includes single or plural probes and can be considered equivalent to the phrase "at least one probe."

As used herein, the term "comprises" means "includes." Thus, "comprising a probe" means "including a probe" without excluding other elements.

It is further to be understood that all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the invention, the following explanations of terms are provided:

Animal: A living multi-cellular vertebrate or invertebrate organism, a category that includes, for example, mammals and birds. The term mammal includes both human and non-human mammals. Similarly, the term "subject" includes both human and veterinary subjects.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample, for example the number of copies of a *S. pneumoniae* nucleic acid, such as a *S. pneumoniae* lytA nucleic acid or fragment thereof. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR; real-time reverse transcriptase PCR (rt RT-PCR); nested PCR; strand displacement amplification (see U.S. Pat. No. 5,744,311); transcription-free isothermal amplification (see U.S. Pat. No. 6,033,881; repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

cDNA (complementary DNA): A piece of DNA lacking internal, non-coding segments (introns) and transcriptional regulatory sequences. cDNA also can contain untranslated regions (UTRs) that are responsible for translational control in the corresponding RNA molecule. cDNA can be synthesized in the laboratory by reverse transcription from RNA, for example an RNA from *S. pneumoniae*, such as an RNA encoding *S. pneumoniae* lytA, psaA, or ply.

Change: To become different in some way, for example to be altered, such as increased or decreased. A detectable change is one that can be detected, such as a change in the intensity, frequency or presence of an electromagnetic signal, such as fluorescence, for example a change in fluorescence of a probe, such as an TAQMAN® probe specific for an *S. pneumoniae* nucleic acid, such as a *S. pneumoniae* lytA nucleic acid, a *S. pneumoniae* psaA nucleic acid, or a *S. pneumoniae* ply nucleic acid. In some examples, the detectable change is a reduction in fluorescence intensity. In some examples, the detectable change is an increase in fluorescence intensity.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions. In some examples, a nucleic acid molecule, such as the probes and primers specific for *S. pneumoniae* lytA, psaA, or ply disclosed herein, are complementary to a *S. pneumoniae* lytA, psaA, or ply nucleic acid molecule or the amplification products of such a nucleic acid molecule.

Detect: To determine if an agent (such as a signal, particular nucleotide, amino acid, nucleic acid molecule, and/or organism) is present or absent, for example *S. pneumoniae*. In some examples, this can further include quantification. For example, use of the disclosed probes in particular examples permits detection of a fluorophore, for example, detection of a signal from a fluorophore, which can be used to determine if a nucleic acid corresponding to nucleic acid of *S. pneumoniae* (such as a *S. pneumoniae* lytA nucleic acid molecule, a *S. pneumoniae* psaA nucleic acid molecule, or a *S. pneumoniae* ply nucleic acid molecule) is present. The detection of a *S. pneumoniae* nucleic acid molecule indicates the presence of *S. pneumoniae* in the sample, for example a *S. pneumoniae* infection in the sample.

Electromagnetic radiation: A series of electromagnetic waves that are propagated by simultaneous periodic variations of electric and magnetic field intensity, and that includes radio waves, infrared, visible light, ultraviolet light, X-rays and gamma rays. In particular examples, electromagnetic radiation is emitted by a laser, which can possess properties of monochromaticity, directionality, coherence, polarization, and intensity. Lasers are capable of emitting light at a particular wavelength (or across a relatively narrow range of wavelengths), for example, so that energy from the laser can excite a donor but not an acceptor fluorophore.

Emission or emission signal: The light of a particular wavelength generated from a source. In particular examples, an emission signal is emitted from a fluorophore after the fluorophore absorbs light at its excitation wavelength(s).

Excitation or excitation signal: The light of a particular wavelength necessary and/or sufficient to excite an electron transition to a higher energy level. In particular examples, an excitation is the light of a particular wavelength necessary and/or sufficient to excite a fluorophore to a state such that the fluorophore will emit a different (such as a longer) wavelength of light then the wavelength of light from the excitation signal.

Fluorophore: A chemical compound, which when excited by exposure to a particular stimulus such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Examples of particular fluorophores that can be used in the S. pneumoniae specific probes and primers disclosed herein are known to those of skill in the art and include those provided in U.S. Pat. No. 5,866,366 to Nazarenko et al., such as 4-acetamido-4'-isothiocyanatostilbene-2,2' disulfonic acid; acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC), -6-carboxy-fluorescein (HEX), and TET (Tetramethyl fluorescein); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (CIBACRON™. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red); riboflavin; rosolic acid and terbium chelate derivatives; LightCycler Red 640; Cy5.5; and Cy56-carboxyfluorescein; boron dipyrromethene difluoride (BODIPY); acridine; stilbene; 6-carboxy-X-rhodamine (ROX); Texas Red; Cy3; Cy5, VIC® (Applied Biosystems); LC Red 640; LC Red 705; and Yakima yellow amongst others.

Other suitable fluorophores include those known to those skilled in the art, for example those available from Molecular Probes (Eugene, Oreg.). In particular examples, a fluorophore is used as a donor fluorophore or as an acceptor fluorophore.

"Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum that overlaps with the emission of the donor fluorophore, such that energy emitted by the donor can excite the acceptor. Ideally, an acceptor fluorophore is capable of being attached to a nucleic acid molecule.

In a particular example, an acceptor fluorophore is a dark quencher, such as Dabcyl, QSY7 (Molecular Probes), QSY33 (Molecular Probes), BLACK HOLE QUENCHERS™ (Glen Research), ECLIPSE™ Dark Quencher (Epoch Biosciences), or IOWA BLACK™ (Integrated DNA Technologies). A quencher can reduce or quench the emission of a donor fluorophore. In such an example, instead of detecting an increase in emission signal from the acceptor fluorophore when in sufficient proximity to the donor fluorophore (or detecting a decrease in emission signal from the acceptor fluorophore when a significant distance from the donor fluorophore), an increase in the emission signal from the donor fluorophore can be detected when the quencher is a significant distance from the donor fluorophore (or a decrease in emission signal from the donor fluorophore when in sufficient proximity to the quencher acceptor fluorophore).

"Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Fluorescence Resonance Energy Transfer (FRET): A spectroscopic process by which energy is passed between an initially excited donor to an acceptor molecule separated by 10-100 Å. The donor molecules typically emit at shorter wavelengths that overlap with the absorption of the acceptor molecule. The efficiency of energy transfer is proportional to the inverse sixth power of the distance (R) between the donor and acceptor ($1/R^6$) fluorophores and occurs without emission of a photon. In applications using FRET, the donor and acceptor dyes are different, in which case FRET can be detected either by the appearance of sensitized fluorescence of the acceptor or by quenching of donor fluorescence. For example, if the donor's fluorescence is quenched it indicates the donor and acceptor molecules are within the Förster radius (the distance where FRET has 50% efficiency, about 20-60 Å), whereas if the donor fluoresces at its characteristic wavelength, it denotes that the distance between the donor and acceptor molecules has increased beyond the Förster radius, such as when a TAQMAN® probe is degraded by Taq polymerase following hybridization of the probe to a target nucleic acid sequence or when a hairpin probe is hybridized to a target nucleic acid sequence. In another example, energy is transferred via FRET between two different fluorophores such that the acceptor molecule can emit light at its characteristic wavelength, which is always longer than the emission wavelength of the donor molecule.

Examples of oligonucleotides using FRET that can be used to detect amplicons include linear oligoprobes, such as Hyb-Probes, 5' nuclease oligoprobes, such as TAQMAN® probes, hairpin oligoprobes, such as molecular beacons, scorpion primers and UniPrimers, minor groove binding probes, and self-fluorescing amplicons, such as sunrise primers.

Hybridization: The ability of complementary single-stranded DNA or RNA to form a duplex molecule (also referred to as a hybridization complex). Nucleic acid hybridization techniques can be used to form hybridization complexes between a probe or primer and a nucleic acid, such as a S. pneumoniae nucleic acid molecule, such as a S. pneumoniae lytA, a psaA, or a ply nucleic acid molecule. For example, a probe or primer (such as any of SEQ ID NOs:3-12) having some homology to a S. pneumoniae nucleic acid molecule will form a hybridization complex with a S. pneumoniae nucleic acid molecule (such as any of SEQ ID NOs:13-15).

Figure 2:
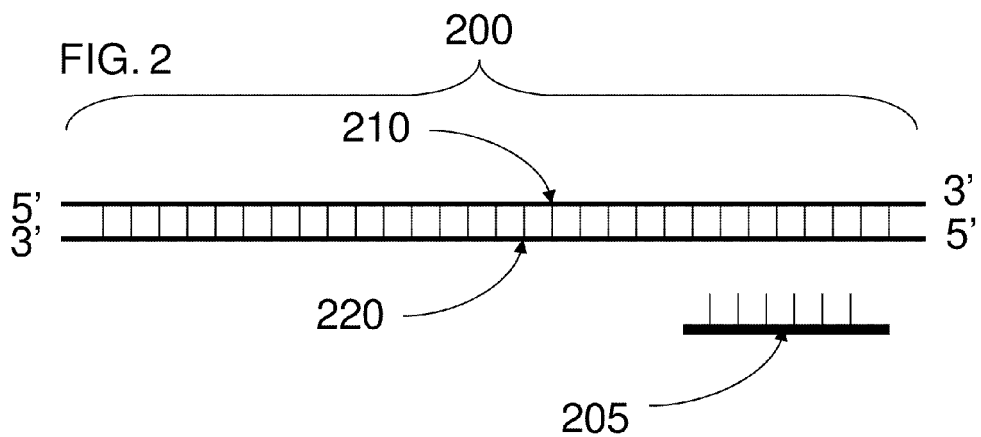
FIG. 2 is a schematic representation of a generalized procedure for hybridizing a S. pneumoniae specific probe to a S. pneumoniae nucleic acid, wherein the S. pneumoniae nucleic acid is initially a double stranded nucleic acid.
Figure 2:
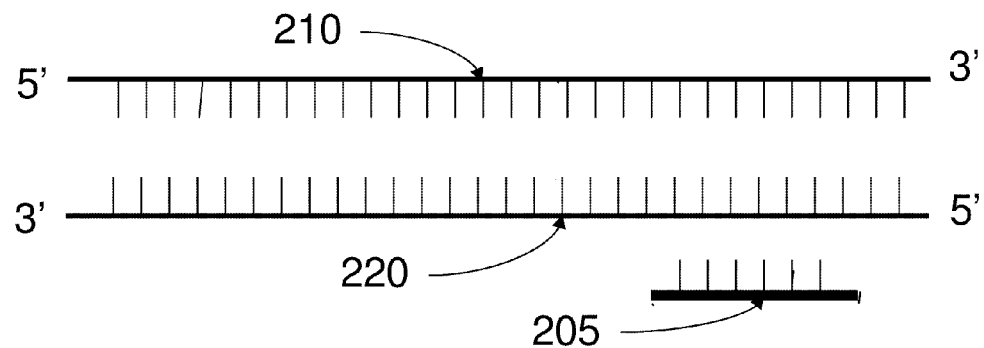
Figure 2:
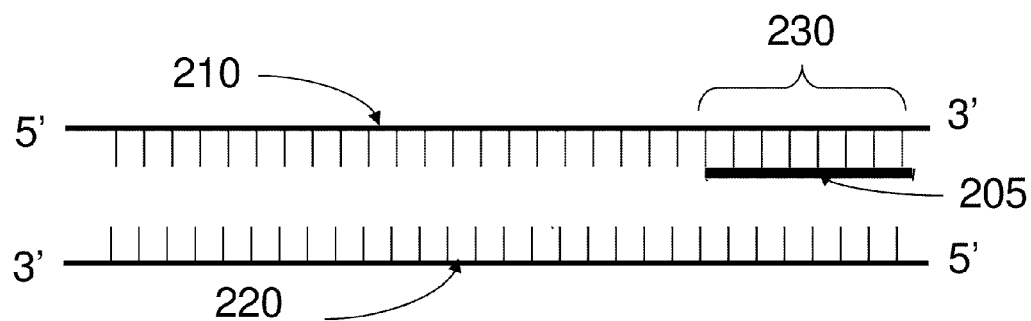

With reference to FIG. 1, the formation of hybridization complex 110 occurs between single stranded probe 105 and single stranded target nucleic acid 100 (such as a S. pneumoniae nucleic acid molecule, for example a lytA, psaA, or ply nucleic acid molecule). With reference to FIG. 2, when target nucleic acid 210 is initially one strand of duplex nucleic acid 200 the duplex must be melted (at least partially) into target nucleic acid 210 and complementary strand 220 for probe 205 to hybridize and form hybridization complex 230.

Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
  Hybridization: 5×SSC at 65° C. for 16 hours
  Wash twice: 2×SSC at room temperature (RT) for 15 minutes each
  Wash twice: 0.5×SSC at 65° C. for 20 minutes each
High Stringency (Detects Sequences that Share at Least 80% Identity)
  Hybridization: 5×-6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (Detects Sequences that Share at Least 50% Identity)
  Hybridization: 6×SSC at RT to 55° C. for 16-20 hours
  Wash at least twice: 2×-3×SSC at RT to 55° C. for 20-30 minutes each.

The probes and primers disclosed herein can hybridize to S. pneumoniae nucleic acid molecules, such as a lytA, psaA, or ply nucleic acid molecule, under low stringency, high stringency, and very high stringency conditions.

Isolated: An "isolated" biological component (such as a nucleic acid) has been substantially separated or purified away from other biological components in which the component naturally occurs, such as other chromosomal and extra-chromosomal DNA, RNA, and proteins. Nucleic acids that have been "isolated" include nucleic acids purified by standard purification methods. The term also embraces nucleic acids prepared by recombinant expression in a host cell as well as chemically synthesized nucleic acids, such as probes and primers, for example S. pneumoniae specific probes and primers disclosed herein. Isolated does not require absolute purity, and can include nucleic acid molecules that are at least 50% isolated, such as at least 75%, 80%, 90%, 95%, 98%, 99%, or even 100% isolated.

Label: An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part, such as a S. pneumoniae specific probe and/or primer. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Nucleic acid (molecule or sequence): A deoxyribonucleotide or ribonucleotide polymer including without limitation, cDNA, mRNA, genomic DNA, and synthetic (such as chemically synthesized) DNA or RNA. The nucleic acid can be double stranded (ds) or single stranded (ss). Where single stranded, the nucleic acid can be the sense strand or the antisense strand. Nucleic acids can include natural nucleotides (such as A, T/U, C, and G), and can include analogs of natural nucleotides, such as labeled nucleotides. In some examples, a nucleic acid is a S. pneumoniae nucleic acid, which can include nucleic acids purified from S. pneumoniae as well as the amplification products of such nucleic acids.

Nucleotide: The fundamental unit of nucleic acid molecules. A nucleotide includes a nitrogen-containing base attached to a pentose monosaccharide with one, two, or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336 to Nazarenko et al. (herein incorporated by reference).

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, and 2,6-diaminopurine amongst others.

Examples of modified sugar moieties, which may be used to modify nucleotides at any position on its structure, include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Primers: Short nucleic acid molecules, such as a DNA oligonucleotide, for example sequences of at least 15 nucleotides, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule (such as a portion of a S. pneumoniae nucleic acid molecule, for example a portion of a lytA, psaA, or ply nucleic acid molecule), wherein the sequence of the primer is specific for the target nucleic acid molecule, for example so that the primer will hybridize to the target nucleic acid molecule under very high stringency hybridization conditions.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50 or more consecutive nucleotides.

In particular examples, a primer is at least 15 nucleotides in length, such as at least 15 contiguous nucleotides complementary to a target nucleic acid molecule. Particular lengths of primers that can be used to practice the methods of the present disclosure (for example, to amplify a region of a S. pneumoniae nucleic acid molecule, such as a portion of a lytA, psaA, or ply nucleic acid molecule) include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 15-60 nucleotides, 15-50 nucleotides, 20-40 nucleotides, 25-50, nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence (such as the S. pneumoniae nucleic acid sequences set forth as SEQ ID NOS: 13-15), for example, by using computer programs intended for that purpose such as Primer (Version 0.5, © 1991, Whitehead Institute for Biomedical Research, Cambridge, Mass.) or PRIMER EXPRESS® Software (Applied Biosystems, AB, Foster City, Calif.).

Methods for preparing and using primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences. In one example, a primer includes a label.

Probe: A probe comprises an isolated nucleic acid capable of hybridizing to a target nucleic acid (such as a S. pneumoniae nucleic acid, for example a S. pneumoniae lytA, psaA, or ply nucleic acid molecule). A detectable label or reporter molecule can be attached to a probe. Typical labels include radioactive isotopes, enzyme substrates, co-factors, ligands, chemiluminescent or fluorescent agents, haptens, and enzymes.

Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally at least 20 nucleotides in length, such as at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, or more contiguous nucleotides complementary to the target nucleic acid molecule, such as 20-60 nucleotides, 30-60 nucleotides, 20-50 nucleotides, 30-50 nucleotides, 20-40 nucleotides, or 20-30 nucleotides.

Polymerizing agent: A compound capable of reacting monomer molecules (such as nucleotides) together in a chemical reaction to form linear chains or a three-dimensional network of polymer chains. A particular example of a polymerizing agent is polymerase, an enzyme which catalyzes the 5' to 3' elongation of a primer strand complementary to a nucleic acid template. Examples of polymerases that can be used to amplify a nucleic acid molecule include, but are not limited to the *E. coli* DNA polymerase I, specifically the Klenow fragment which has 3' to 5' exonuclease activity, Taq polymerase, reverse transcriptase (such as HIV-1 RT), *E. coli* RNA polymerase, and wheat germ RNA polymerase II.

The choice of polymerase is dependent on the nucleic acid to be amplified. If the template is a single-stranded DNA molecule, a DNA-directed DNA or RNA polymerase can be used; if the template is a single-stranded RNA molecule, then a reverse transcriptase (such as an RNA-directed DNA polymerase) can be used.

Quantitating a nucleic acid molecule: Determining or measuring a quantity (such as a relative quantity) of nucleic acid molecules present, such as the number of amplicons or the number of nucleic acid molecules present in a sample. In particular examples, it is determining the relative amount or actual number of nucleic acid molecules present in a sample, such as *S. pneumoniae* nucleic acid molecules present in a sample.

Quenching of fluorescence: A reduction of fluorescence. For example, quenching of a fluorophore's fluorescence occurs when a quencher molecule (such as the fluorescence quenchers listed above) is present in sufficient proximity to the fluorophore that it reduces the fluorescence signal (for example, prior to the binding of a probe to an *S. pneumoniae* nucleic acid sequence, when the probe contains a fluorophore and a quencher).

Real-time PCR: A method for detecting and measuring products generated during each cycle of a PCR, which are proportionate to the amount of template nucleic acid prior to the start of PCR. The information obtained, such as an amplification curve, can be used to determine the presence of a target nucleic acid (such as a *S. pneumoniae* nucleic acid) and/or quantitate the initial amounts of a target nucleic acid sequence. Exemplary procedures for real-time PCR can be found in "Quantitation of DNA/RNA Using Real-Time PCR Detection" published by Perkin Elmer Applied Biosystems (1999) and to PCR Protocols (Academic Press New York, 1989).

Figure 4:
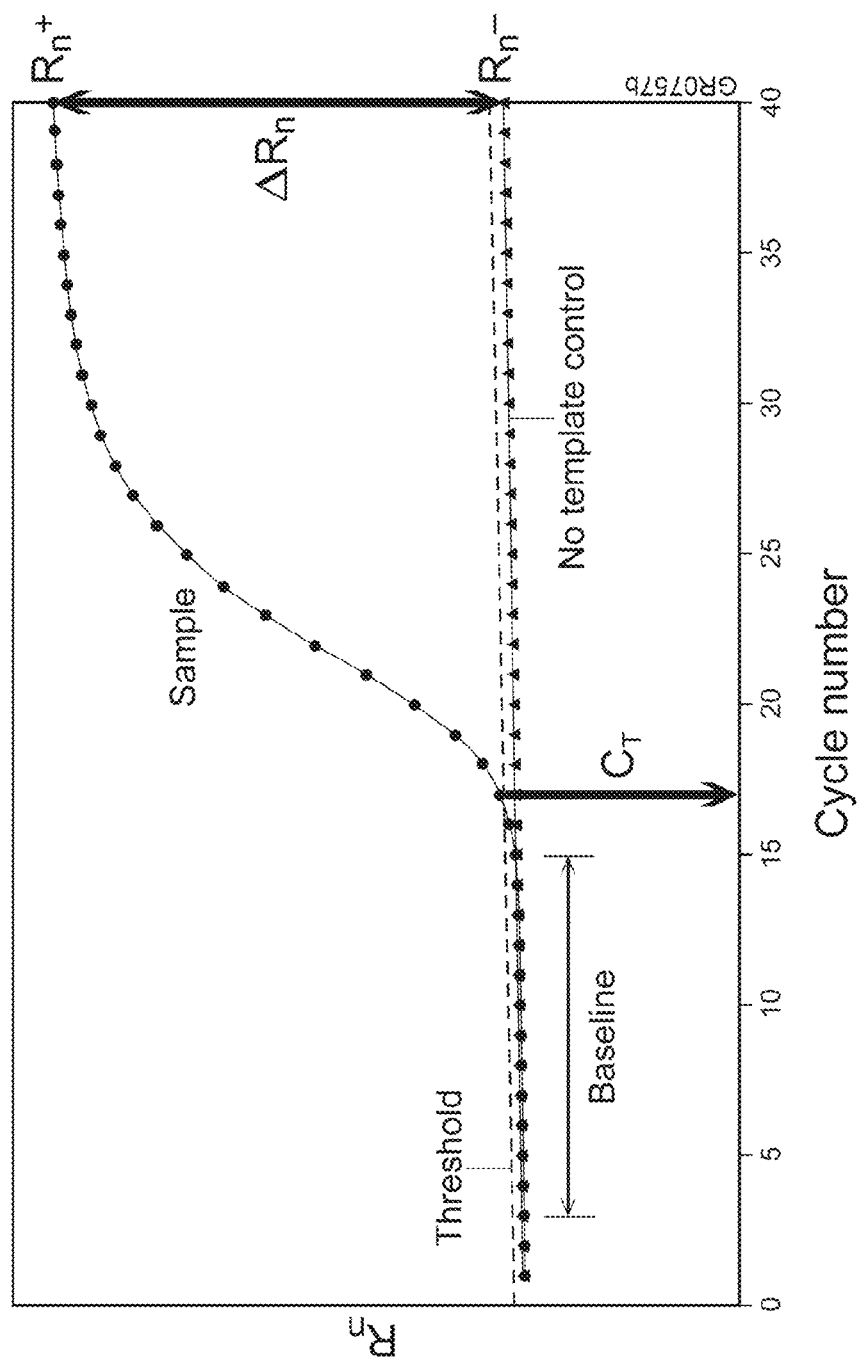
FIG. 4 is a graph of theoretical data generated from real-time polymerase chain reaction (real-time PCR) using TAQMAN® probes.

In some examples, the amount of amplified target nucleic acid (such as a *S. pneumoniae* nucleic acid molecule for example a *S. pneumoniae* lytA, psaA, or ply nucleic acid molecule) is detected using a labeled probe, such as a probe labeled with a fluorophore, for example a TAQMAN® probe. In this example, the increase in fluorescence emission is measured in real-time, during the course of the real-time PCR. This increase in fluorescence emission is directly related to the increase in target nucleic acid amplification (such as *S. pneumoniae* nucleic acid amplification). In some examples, the change in fluorescence (dRn) is calculated using the equation $dRn=Rn^+ - Rn^-$, with $Rn^+$ being the fluorescence emission of the product at each time point and $Rn^-$ being the fluorescence emission of the baseline. The dRn values are plotted against cycle number, resulting in amplification plots for each sample as illustrated in FIG. 4. With reference to FIG. 4, the threshold value (CO is the PCR cycle number at which the fluorescence emission (dRn) exceeds a chosen threshold, which is typically 10 times the standard deviation of the baseline (this threshold level can, however, be changed if desired).

The threshold cycle is when the system begins to detect the increase in the signal associated with an exponential growth of PCR product during the log-linear phase. This phase provides information about the reaction. The slope of the log-linear phase is a reflection of the amplification efficiency. The efficiency of the reaction can be calculated by the following equation: $E=10^{(-1/slope)}-1$. The efficiency of the PCR should be 90-100% meaning doubling of the amplicon at each cycle. This corresponds to a slope of −3.1 to −3.6 in the $C_t$ vs. log-template amount standard curve. In order to obtain accurate and reproducible results, reactions should have efficiency as close to 100% as possible (meaning a two-fold increase of amplicon at each cycle).

Sample: A sample, such as a biological sample, is a sample obtained from a plant or animal subject. As used herein, biological samples include all clinical samples useful for detection *S. pneumoniae* infection in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; bone marrow aspirates; middle ear fluids, bronchoalveolar levage, tracheal aspirates, sputum, nasopharyngeal aspirates, oropharyngeal aspirates, or saliva. In particular embodiments, the biological sample is obtained from an animal subject, such as in the form of middle ear fluids, bronchoalveolar levage, tracheal aspirates, sputum, nasopharyngeal aspirates, oropharyngeal aspirates, or saliva.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

```
                          1                   20
   Target Sequence:     atggtggacccggtgggctt (SEQ ID No: 1)
                        | ||  ||| ||||  ||||  |
   Identified Sequence: acgggggatccggcgggcct (SEQ ID NO: 2)
```

One indication that two nucleic acid molecules are closely related is that the two molecules hybridize to each other under stringent conditions. Stringent conditions are sequence-dependent and are different under different environmental parameters.

The nucleic acid probes and primers disclosed herein are not limited to the exact sequences shown, as those skilled in the art will appreciate that changes can be made to a sequence, and not substantially affect the ability of the probe or primer to function as desired. For example, sequences having at least 80%, at least 90%, at least 95%, at least 96%, at least 97%, at least 98%, or at least 99%, such as 100% sequence identity to any of SEQ ID NOs:3-12 are provided herein. One of skill in the art will appreciate that these sequence identity ranges are provided for guidance only; it is possible that probes and primer can be used that fall outside these ranges.

Signal: A detectable change or impulse in a physical property that provides information. In the context of the disclosed methods, examples include electromagnetic signals such as light, for example light of a particular quantity or wavelength. In certain examples, the signal is the disappearance of a physical event, such as quenching of light.

*Streptococcus pneumoniae* N-acetylmuramoyl-L-alanine amidase (lytA): The lytA-encoded autolysin of *S. pneumoniae*. As used herein "lytA" refers to the nucleotide sequence of lytA, thus a probe or primer for lytA, such as those disclosed herein, is capable of hybridizing to the nucleotide sequence of lytA, such as the lytA nucleotide sequence given below (or the complement thereof). An exemplary nucleotide sequence of lytA as found at GENBANK® Accession number AE005672 on May 7, 2007 is shown below:

```
                                          (SEQ ID NO: 13)
ttatttactgtaatcaagccatctggctctactgtgaattctggcttgt ctgccagtgttccgtctggtttgaggtagtaccagcctgttccgtccgct gactggataaaggcatttgataccatggcgccttctttagcgtctaagta gtaccaagtgtccttgtacttgacccagcctgtcttcatggcaccttctt cgttgaaatagtaccacttatcagcgattttcttccagcctgtagccatt tcgcctgagttgtcgaaccagtaccagttgccgtctgtgtgcttcctcca gcggtctgcaagcatatagcctgaactgtcaaagtagtaccaagtgccat tgattttctcaaacttgtcttttggataagagccgtctgaatgtacgtac cagtagccagtgtcattcttctgccagcctgtttcaatcgtcaagccgtt ctcaatatcatgcttaaactgctcacggctaatgcccatttagcaagat atggataagggtcaacgtggtctgagtggttgtttggttggttattcgtg caatactcgtgcgttttaattccagctaaactccctgtatcaagcgtttt cggcaaacctgcttcatctgctagattgcgtaagagttcgatataaaggc ggtagtccgtcatgaactcttctttggttgaatggctttcaatcagttca accgctgcataggctctcagcattccaaccgcccccaacgtcccaggcacc attatcaacaggtcctacctgcatgatgcaaccgttcccaacaatgtgcg agaaaaacctaattctgggtctttccgccagtgataatccgcttcattc tgtacggttgaatgcggattcccagttgagtgtgcgtgtacttgcctata tggttgcacgccgacttgaggcaaatctgttcttaatttactcacattaa tttccat
```

*Streptococcus pneumoniae* pneumolysin (ply): A virulence factor of *S. pneumoniae*, is one of the members of thiol-activated cytolysins (TACYs) consisting of four domains. As used herein "ply" refers to the nucleotide sequence of ply, thus a probe or primer for ply, such as those disclosed herein, is capable of hybridizing to the nucleotide sequence of ply, such as the ply nucleotide sequence given below (or the complement thereof). An exemplary nucleotide sequence of ply as found at GENBANK® Accession number AE008539 on May 7, 2007 is shown below:

```
                                          (SEQ ID NO: 14)
ctagtcattttctaccttatcctctacctgaggatagagagttgttcccc aaatagaaatcgtccgcttacgcactagtggcaaatcggttttttcataa accgtacgccaccattcccaggcaagcccggtacactctctaattttgac agagagattacgaacattccctttaaaggaatactagtggtaaagtgag ccgtcaaatcctgcccatttctgtcccaagccttaggagtcaagacttcc ttaccttgatgatcataggataattcatcccaagtaatataatattgggc aacataggcaccactatgatccagcagtaaatctccgtttctgtaagctg taaccttagtctcaacatagtctgtactgttttgaaaggtcgcaactaca ttgtcacgtaaaaaagaagttgtataggaaatcggcaagcctggatgatc tgctgtaaagcgactgccttcttgaatcaagtcctctaccatatccacct tgcctgttacaactcgggcacccgaacttgggtcgcccctaaaataacc gccttcacttctgtattgtccaaaatctgcttccactctgtctgaggagc taccttgactccttttatcaaagcttcaaaagcagcctctacttcatcac tcttactcgtggtttccaacttgagatagacttggcgcccataagcaaca ctcgaaatatagaccaaaggacgctctgcagaaattcctctctgttttaa atcctctaccgttacagtatcttgaaacacatctcctggatttttaacag cgtctacgctgactgtataataaatctgcttaaaattaacaatctgaatc tgcttttcacctgaattggacagagttaaaatcaatatcaagagaattccc tgtcttttcaaagtcagaaccaaacttgaccttgagttgttccatgctgt gagccgttatttttcatactgcattctagctgggacattattgacctga ccataatcttgatgccacttagccaacaaatcgtttaccgctccgcgaac acttgaattgctgggtcttccacttggagaaagctatcgctacttgcca aaccaggcaaatcaatactataagtcatcggagcacgatcaaccgcaaga agagtgggattattctctaacaaggtctcatccactacgagaagtgctcc aggatagaggcgactgtcgttggtagctgttacagaaatatcacttgtat ttgtcgacaagctccgcttctttctttcgataacaacaaactcatcgggt agctgattaccctctttgatgaaacgattttcaatactttctccctgatg ggtcaagagtttcttttatcgtaattcatagctagtataaagtcattta ctgctttatttgccat
```

*Streptococcus pneumoniae* surface adhesin A precursor (psaA): psaA encodes a 37-kDa pneumococcal lipoprotein which is part of an ABC Mn(II) transport complex. As used herein "psaA" refers to the nucleotide sequence of psaA, thus a probe or primer for psaA, such as those disclosed herein, is capable of hybridizing to the nucleotide sequence of psaA, such as the psaA nucleotide sequence given below (or the complement thereof). An exemplary nucleotide sequence of psaA as found at GENBANK®Accession number U53509 on May 7, 2007 is shown below:

(SEQ ID NO: 15)
```
tactgcttcagttttgggactctttattggctatagttttaatgttgcgg
caggttctagtatcgtgcttacagctgctagtttctttctcattagcttc
tttatcgctcccaaacaacgatatttgaaactgaaaaataaacatttgtt
aaaataaggggcaaagccctaataaattggaggatctaatgaaaaaatta
ggtacattactcgttctctttctttctgcaatcattcttgtagcatgtgc
tagcggaaaaaagatacaacttctggtcaaaaactaaaagttgttgcta
caaactcaatcatcgctgatattactaaaaatattgctggtgacaaaatt
gaccttcatagtatcgttccgattgggcaagacccacacgaatacgaacc
acttcctgaagacgttaagaaaacttctgaggctgatttgattttctata
acggtatcaaccttgaaacaggtggcaatgcttggtttacaaaattggta
gaaaatgccaagaaaactgaaaacaaagactacttcgcagtcagcgacgg
cgttgatgttatctaccttgaaggtcaaatgaaaaaggaaaagaagacc
cacacgcttggcttaaccttgaaaacggtattattttttgctaaaaatatc
gccaaacaattgagcgccaaagaccctaacaataaagaattctatgaaaa
aaatctcaaagaatatactgataagttagacaaacttgataaagaaagta
aggataaatttaataagatccctgctgaaaagaaactcattgtaaccagc
gaaggagcattcaaatacttctctaaagcctatggtgtcccaagtgccta
catctgggaaatcaatactgaagaagaaggaactcctgaacaaatcaaga
ccttggttgaaaaacttcgccaaacaaaagttccatcactctttgtagaa
tcaagtgtggatgaccgtccaatgaaaactgtttctcaagacacaaacat
cccaatctacgcacaaatctttactgactctatcgcagaacaaggtaaag
aaggcgacagctactacagcatgatgaaatacaaccttgacaagattgct
gaaggattggcaaaataagcctctgaaaaacgtcattctcatgtgagctg
gcgttttttctatgcccacatttccggtcaaatcattggaaaattctgac
tgtttcagatacaatggaagaaaaagattggagtatcctatggtaactt
ttctcggaaatcctgtgagctttacaggtaaacaactacaagtcggcgac
aaggcgcttgattttctcttactacaaca
```

Figure 3:
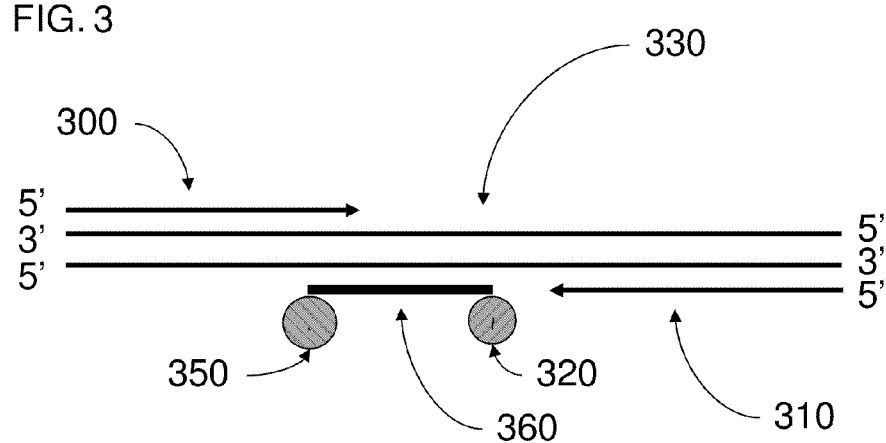
FIG. 3 is a schematic representation of a generalized procedure for hybridizing and detecting S. pneumoniae using a S. pneumoniae specific TAQMAN® probe.
Figure 3:
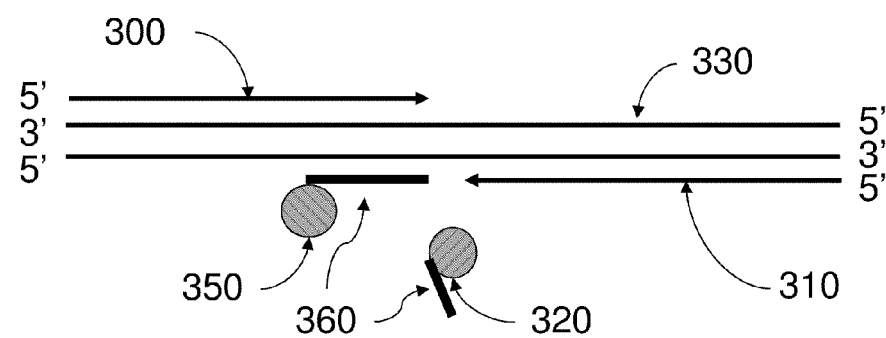
Figure 3:
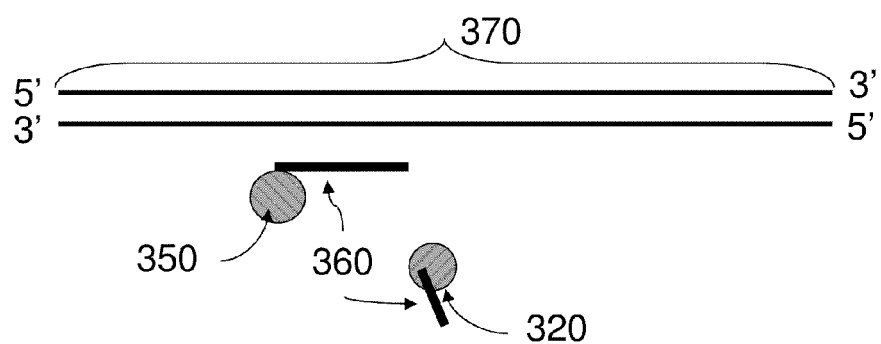

TAQMAN® PCR: With reference to FIG. 3, TAQMAN® probe 360 that typically contains reporter 320 (such as a short-wavelength fluorophore, for example 6-carboxyfluorescein (FAM)) and quencher 350 (such as a long-wavelength fluorophore, for example BLACKHOLE QUENCHER™ 1 (BHQ™1)) is selected to bind to one strand of target nucleic acid 330. When irradiated energy is transferred (via FRET) from reporter 320 to quencher 350 on the other end of intact TAQMAN® probe 360. Thus, the close proximity of reporter 320 and quencher 350 prevents detection of any signal while TAQMAN® probe 360 is intact. When Taq polymerase replicates target nucleic acid 330 using primers 300, 301 on which TAQMAN® probe 360 is bound, polymerase 380's 5' exonuclease activity cleaves TAQMAN® probe 360. Upon degradation, FRET is interrupted, ending the activity of quencher 350. Reporter 320 starts to emit signal, which increases in each cycle proportional to the rate of TAQMAN® probe 360 cleavage. Accumulation of PCR product 370 is detected by monitoring the increase in signal of reporter 320. Because the cleavage occurs only if TAQMAN® probe 360 hybridizes to target nucleic acid 330, the origin of the detected fluorescence is specific amplification. The process of hybridization and cleavage does not interfere with the exponential accumulation of PCR product 370.

Target nucleic acid molecule: A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule (which can include RNA such as *S. pneumoniae* RNA, or DNA such as *S. pneumoniae* DNA, for example a *S. pneumoniae* lytA, psaA or ply DNA), the amplification of which is intended. Purification or isolation of the target nucleic acid molecule, if needed, can be conducted by methods known to those in the art, such as by using a commercially available purification kit or the like. In one example, a target nucleic molecule is a *S. pneumoniae* nucleic acid sequence.

II. Overview of Several Embodiments

Accurate diagnosis of pneumococcal disease has been frequently hampered not only by the difficulties in obtaining isolates of the organism from patient specimens, but also by the misidentification of pneumococcus-like viridans streptococci species (P-LVS) as *Streptococcus pneumoniae* (*S. pneumoniae*). In order to achieve an accurate diagnosis, an assay should be both sensitive and highly specific for diagnosis of the disease, such as the diagnosis of a *S. pneumoniae* infection. Disclosed herein are probes and primers designed for detection *S. pneumoniae* by detecting of specific sequence regions of the *S. pneumoniae* lytA, ply, and psaA genes, for example in real-time PCR assays, such as in multiplex real-time PCR assays. When used in representative real-time PCR assays, the probes and primers disclosed herein demonstrated both high sensitivity and high specificity for *S. pneumoniae* and represent a significant advancement over the probes and primers typically used for the detection of *S. pneumoniae*, such as the probes and primers described by Corless et al. (Corless et al., *J. Clin. Microbiol.* 39:1553-1558, 2001) and McAvin et al. (McAvin et al., *J. Clin. Microbiol.* 39:3446-3451, 2001).

A direct comparison (using real-time PCR) of the disclosed probes and primers (lytA-CDC, psaA-CDC, and ply-CDC) with the probes and primers described by Corless et al. and McAvin et al. (lytA-McAvin and ply-Corless) over a panel of isolates consisting of: 67 *S. pneumoniae* (44 different serotypes and 3 non-encapsulated *Streptococcus pneumoniae* from conjunctivitis outbreaks), and 104 non-pneumococcal isolates demonstrated that the probes and primers disclosed herein, such as the probes and primers specific for *S. pneumoniae* lytA, ply, and psaA, were superior in discriminating between *S. pneumoniae* isolates and non-*S. pneumoniae* isolates. The disclosed probes, as well as those described by Corless et al. and McAvin et al., detected the 67 *S. pneumoniae* isolates. However, the disclosed *S. pneumoniae* lytA and psaA specific probes and primers demonstrated superior specificity for *S. pneumoniae* over the assays described by Corless et al. and McAvin et al. For example, the probes and primers described by Corless et al. and McAvin et al. registered false positives, and could result in a misdiagnosis of *S. pneumoniae* in some instances. Both the lytA-CDC and the psaA-CDC real-time PCR assays were highly specific, showing no amplification with P-LVS isolates. The newly developed methods described herein provide assays with not only high sensitivity but also improve specificity over those currently in use. The improvement in specificity allows their use with specimens from non-sterile sites, as well as sterile sites making them suitable for both diagnosis and for use in carriage studies.

Figure 5:
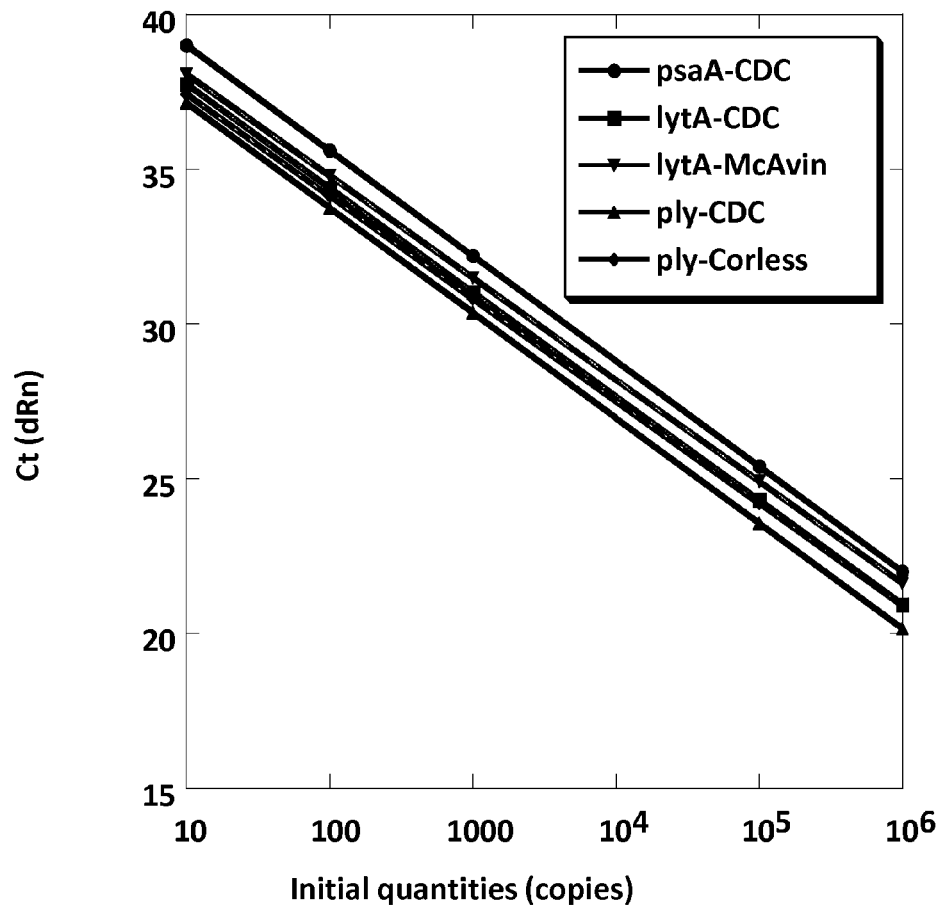
FIG. 5 is a graph of S. pneumoniae specific TAQMAN® probes used in a multiplex real-time PCR assay, showing the efficiency of the indicated probe and primer sets.

Both the lytA-CDC and psaA-CDC assays, and particularly the lytA-CDC assay, represent an improvement in specificity over what is currently available and should therefore be considered as the assays of choice for the detection of pneumococcal DNA, particularly when upper respiratory P-LVS might be present in the clinical specimen. Use of the disclosed probes and primers for the diagnosis of S. pneumoniae will lead to a decrease in misdiagnosis, improve patient management, and improve monitoring of S. pneumoniae outbreaks. In addition, as demonstrated by example 5 (see FIG. 5) the disclosed probes and primers are ideal for use in multiplex PCR assays for simultaneous detection of various pathogens. The S. pneumoniae specific probes and primers disclosed herein, such as the lytA, psaA, and ply specific primers and probes provide high specificity in a respiratory platform multiplexed with primers and probes for detection of other respiratory pathogens. This potential for multiplexing and the speed of performance make these assays beneficial tools for molecular detection and epidemiologic carriage studies.

Probes and Primers

Probes capable of hybridizing to and detecting the presence of S. pneumoniae nucleic acid molecules, such as S. pneumoniae lytA nucleic acid molecules, S. pneumoniae psaA nucleic acid molecules, or S. pneumoniae ply nucleic acid molecules, are disclosed. In some embodiments, such probes are specific for S. pneumoniae, in that they do not specifically hybridize to sequences from other organisms, such as other bacteria. The disclosed probes are between 20 and 40 nucleotides in length, such as 20, 21, 22, 23, 24, 25, 26, 27, 28 29, 30, 31, 32, 32, 34, 35, 36, 37, 38, 39, or 40 nucleotides in length and are capable of hybridizing to the S. pneumoniae nucleic acid molecule, such as the S. pneumoniae lytA sequence set forth as SEQ ID NO: 13, the S. pneumoniae psaA sequence set forth as SEQ ID NO: 14, or the S. pneumoniae ply sequence set forth as SEQ ID NO: 15. In several embodiments, a probe is capable of hybridizing under very high stringency conditions to a S. pneumoniae nucleic acid sequence set forth as SEQ ID NO: 13. In other embodiments, a probe is capable of hybridizing under very high stringency conditions to a S. pneumoniae nucleic acid sequence set forth as SEQ ID NO: 14. In still other embodiments, a probe is capable of hybridizing under very high stringency conditions to a S. pneumoniae nucleic acid sequence set forth as SEQ ID NO: 15.

In several embodiments, a probe capable of hybridizing to a S. pneumoniae nucleic molecule contains a nucleic acid sequence that is at least 95% identical, such as at least 96%, at least 97%, at least 98%, at least 99%, or even 100% identical, to the nucleotide sequence set forth as one of GCCGAAAACGCTTGATACAGGGAG (SEQ ID NO: 5), TGCCGAAAACGCTTGATACAGGGAG (SEQ ID NO: 6), CTAGCACATGCTACAAGAATGATTGCAGAAAGAAA (SEQ ID NO: 9), or CTCAAGTTGGAAACCACGAGTAAGAGTGATGAA (SEQ ID NO: 12).

In several embodiments, a probe capable of hybridizing to a S. pneumoniae lytA nucleic molecule contains a nucleic acid sequence that is at least 95% identical, such as at least 96%, at least 97%, at least 98%, at least 99%, or even 100% identical, to the nucleotide sequence set forth as SEQ ID NO: 5, or SEQ ID NO: 6. In several embodiments, a probe capable of hybridizing to a S. pneumoniae lytA nucleic acid molecule consists essentially of a nucleic acid sequence set forth as SEQ ID NO: 5, or SEQ ID NO: 6.

In several embodiments, a probe capable of hybridizing to a S. pneumoniae psaA nucleic molecule contains a nucleic acid sequence that is at least 95% identical, such as at least 96%, at least 97%, at least 98%, at least 99%, or even 100% identical, to the nucleotide sequence set forth as SEQ ID NO: 9. In several embodiments, a probe capable of hybridizing to a S. pneumoniae psaA nucleic acid molecule consists essentially of a nucleic acid sequence set forth as SEQ ID NO: 9.

In several embodiments, a probe capable of hybridizing to a S. pneumoniae ply nucleic molecule contains a nucleic acid sequence that is at least 95% identical, such as at least 96%, at least 97%, at least 98%, at least 99%, or even 100% identical, to the nucleotide sequence set forth as SEQ ID NO: 12. In several embodiments, a probe capable of hybridizing to a S. pneumoniae ply nucleic acid molecule consists essentially of a nucleic acid sequence set forth as SEQ ID NO: 12.

In some embodiments, the probe is detectably labeled, either with an isotopic or non-isotopic label, alternatively the target nucleic acid (such as a S. pneumoniae nucleic acid molecule, for example a S. pneumoniae lytA nucleic acid molecule such as set forth as SEQ ID NO: 13 or a subsequence thereof, a S. pneumoniae psaA nucleic acid molecule such as set forth as SEQ ID NO: 14 or a subsequence thereof, or a S. pneumoniae ply nucleic acid molecule such as set forth as SEQ ID NO: 15 or a subsequence thereof) is labeled. Non-isotopic labels can include a fluorescent or luminescent molecule, biotin, an enzyme or enzyme substrate or a chemical. Such labels are preferentially chosen such that the hybridization of the probe with target nucleic acid (such as a S. pneumoniae nucleic acid molecule, for example a S. pneumoniae lytA, a S. pneumoniae psaA, or a S. pneumoniae ply nucleic acid molecule or subsequence thereof) can be detected. In some examples, the probe is labeled with a fluorophore. Examples of suitable fluorophore labels are given above. In some examples, the fluorophore is a donor fluorophore. In other examples, the fluorophore is an accepter fluorophore, such as a fluorescence quencher. In some examples, the probe includes both a donor fluorophore and an accepter fluorophore, for example a donor fluorophore such as a FAM and an acceptor fluorophore such as a BLACK HOLE® quencher. Appropriate donor/acceptor fluorophore pairs can be selected using routine methods. In one example, the donor emission wavelength is one that can significantly excite the acceptor, thereby generating a detectable emission from the acceptor. In some examples, the probe is modified at the 3'-end to prevent extension of the probe by a polymerase.

In particular examples, the acceptor fluorophore (such as a fluorescence quencher) is attached to the 3' end of the probe and the donor fluorophore is attached to a 5' end of the probe. In other examples, the acceptor fluorophore (such as a fluorescence quencher) is attached to the 5' end of the probe and the donor fluorophore is attached to a 3' end of the probe. In another particular example, the acceptor fluorophore (such as a fluorescence quencher) is attached to a modified nucleotide (such as a T) and the donor fluorophore is attached to a 5' end of the probe.

Primers capable of hybridizing to and directing the amplification of a S. pneumoniae nucleic acid molecule are disclosed. In some embodiments, such primers are specific for S. pneumoniae, in that they do not specifically hybridize to nucleic acid sequences from other organisms, such as other bacteria. The primers disclosed herein are between 15 to 40 nucleotides in length, such as 15, 16, 17, 18, 19, 20, 21, 22, 23, 24, 25, 26, 27, 28, 29, 30, 31, 32, 33, 34, 35, 36, 37, 38, 39, or even 40 nucleotides in length.

In several embodiments, a primer is capable of hybridizing under very high stringency conditions to a *S. pneumoniae* lytA nucleic acid sequence, such as a *S. pneumoniae* lytA sequence set forth as SEQ ID NO: 13, and directing the amplification of the *S. pneumoniae* lytA nucleic acid molecule, for example amplification of SEQ ID NO: 13 or a subsequence thereof. In several embodiments, a primer is capable of hybridizing under very high stringency conditions to a *S. pneumoniae* psaA nucleic acid sequence, such as a *S. pneumoniae* psaA sequence set forth as SEQ ID NO: 14, and directing the amplification of the *S. pneumoniae* psaA nucleic acid molecule, for example amplification of SEQ ID NO: 14 or a subsequence thereof. In several embodiments, a primer is capable of hybridizing under very high stringency conditions to a *S. pneumoniae* ply nucleic acid sequence, such as a *S. pneumoniae* ply sequence set forth as SEQ ID NO: 15, and directing the amplification of the *S. pneumoniae* ply nucleic acid molecule, for example amplification of SEQ ID NO: 15 or a subsequence thereof.

In several embodiments, a primer capable of hybridizing to and directing the amplification of a *S. pneumoniae* nucleic acid molecule contains a nucleic acid sequence that is at least 95% identical, such as at least 96%, at least 97%, at least 98%, at least 99%, or even 100% identical, to the nucleic acid sequence set forth as

```
ACGCAATCTAGCAGATGAAGCA,        (SEQ ID NO: 3)

TCGTGCGTTTTAATTCCAGCT,         (SEQ ID NO: 4)

GCCCTAATAAATTGGAGGATCTAATGA,   (SEQ ID NO: 7)

GACCAGAAGTTGTATCTTTTTTTCCG,    (SEQ ID NO: 8)

GCTTATGGGCGCCAAGTCTA,          (SEQ ID NO: 10)
or

CAAAGCTTCAAAAGCAGCCTC TA.      (SEQ ID NO: 11)
```

In several embodiments, a primer capable of hybridizing to a *S. pneumoniae* nucleic acid molecule consists essentially of a nucleic acid sequence set forth as SEQ ID NO: 3, SEQ ID NO: 4, SEQ ID NO: 7, SEQ ID NO: 8, SEQ ID NO: 10, or SEQ ID NO: 11. In several embodiments, a primer capable of hybridizing to and directing the amplification of a *S. pneumoniae* lytA nucleic acid molecule contains a nucleic acid sequence that is at least 95% identical, such as at least 96%, at least 97%, at least 98%, at least 99%, or even 100% identical, to the nucleic acid sequence set forth as SEQ ID NO: 3 or SEQ ID NO: 4. In several embodiments, a primer capable of hybridizing to and directing the amplification of a *S. pneumoniae* lytA nucleic acid molecule consists essentially of a nucleic acid sequence set forth as SEQ ID NO: 3 or SEQ ID NO: 4. In several embodiments, a primer capable of hybridizing to and directing the amplification of a *S. pneumoniae* psaA nucleic acid molecule contains a nucleic acid sequence that is at least 95% identical, such as at least 96%, at least 97%, at least 98%, at least 99%, or even 100% identical, to the nucleic acid sequence set forth as SEQ ID NO: 7 or SEQ ID NO: 8. In several embodiments, a primer capable of hybridizing to and directing the amplification of a *S. pneumoniae* psaA nucleic acid molecule consists essentially of a nucleic acid sequence set forth as SEQ ID NO: 7 or SEQ ID NO: 8. In several embodiments, a primer capable of hybridizing to and directing the amplification of a *S. pneumoniae* ply nucleic acid molecule contains a nucleic acid sequence that is at least 95% identical, such as at least 96%, at least 97%, at least 98%, at least 99%, or even 100% identical, to the nucleic acid sequence set forth as SEQ ID NO: 10 or SEQ ID NO: 11. In several embodiments, a primer capable of hybridizing to and directing the amplification of a *S. pneumoniae* ply nucleic acid molecule consists essentially of a nucleic acid sequence set forth as SEQ ID NO: 10 or SEQ ID NO: 11.

In certain embodiments, the primers are a set of primers, such as a pair of primers, capable of hybridizing to and amplifying a *S. pneumoniae* nucleic acid molecule, such as a *S. pneumoniae* lytA, a *S. pneumoniae* psaA, or a *S. pneumoniae* ply nucleic acid molecule. Such a set of primers includes at least one forward primer and a least one reverse primer, where the primers are specific for the amplification of a *S. pneumoniae* nucleic acid molecule such as a *S. pneumoniae* lytA, a *S. pneumoniae* psaA, or a *S. pneumoniae* ply nucleic acid molecule. In some embodiments, the set of primers includes at least one pair of primers specific for the amplification a *S. pneumoniae* lytA, a *S. pneumoniae* psaA, or a *S. pneumoniae* ply nucleic acid molecule, for example such a set of primers could include a pair of primers for the amplification of *S. pneumoniae* lytA, a pair of primers for the amplification of *S. pneumoniae* psaA, or a pair of primers for the amplification of *S. pneumoniae* ply, or any combination thereof, such as a pair of primers for the amplification of *S. pneumoniae* lytA and a pair of primers for the amplification of *S. pneumoniae* psaA, a pair of primers for the amplification of *S. pneumoniae* lytA and a pair of primers for the amplification of *S. pneumoniae* ply, a pair of primers for the amplification of *S. pneumoniae* ply and a pair of primers for the amplification of *S. pneumoniae* psaA, or even a pair of primers for the amplification of *S. pneumoniae* lytA, a pair of primers for the amplification of *S. pneumoniae* psaA, and a pair of primers for the amplification of *S. pneumoniae* ply.

In some examples, the set of primers includes a pair of primers that is specific for the amplification of a *S. pneumoniae* nucleic acid molecule that includes a portion of the nucleic acid sequence of the *S. pneumoniae* lytA gene, such as the nucleic acid sequence set forth as SEQ ID NO: 13. In certain examples, the pair of primers is specific for the amplification of a *S. pneumoniae* lytA nucleic acid molecule and includes a forward primer at least 95% identical to SEQ ID NO: 3, such as at least 96%, at least 97%, at least 98%, at least 99%, or even 100% identical to SEQ ID NO: 3, and a reverse primer at least 95% identical to SEQ ID NO: 4, such as at least 96%, at least 97%, at least 98%, at least 99%, or even 100% identical to SEQ ID NO: 4.

In some examples, the set of primers includes a pair of primers that is specific for the amplification of a *S. pneumoniae* nucleic acid molecule that includes a portion of the nucleic acid sequence of the *S. pneumoniae* psaA gene, such as the nucleic acid sequence set forth as SEQ ID NO: 14. In certain examples, the pair of primers is specific for the amplification of a *S. pneumoniae* lytA nucleic acid molecule and includes a forward primer at least 95% identical to SEQ ID NO: 7, such as at least 96%, at least 97%, at least 98%, at least 99%, or even 100% identical to SEQ ID NO: 7, and a reverse primer at least 95% identical to SEQ ID NO: 8, such as at least 96%, at least 97%, at least 98%, at least 99%, or even 100% identical to SEQ ID NO: 8.

In some examples, the set of primers includes a pair of primers that is specific for the amplification of a *S. pneumoniae* nucleic acid molecule that includes a portion of the nucleic acid sequence of the *S. pneumoniae* ply gene, such as the nucleic acid sequence set forth as SEQ ID NO: 14. In certain examples, the pair of primers is specific for the amplification of a *S. pneumoniae* ply nucleic acid molecule and includes a forward primer at least 95% identical to SEQ ID NO: 10, such as at least 96%, at least 97%, at least 98%, at least 99%, or even 100% identical to SEQ ID NO: 10, and a reverse primer at least 95% identical to SEQ ID NO: 11, such as at least 96%, at least 97%, at least 98%, at least 99%, or even 100% identical to SEQ ID NO: 11.

Although exemplary probes and primers are provided in SEQ ID NOS:3-12, the primer and/or probe sequence can be varied slightly by moving the probes a few nucleotides upstream or downstream from the nucleotide positions that they hybridize to on the *S. pneumoniae* nucleic molecule acid, provided that the probe and/or primer is still specific for the *S. pneumoniae* nucleic acid sequence, for example specific for SEQ ID NO: 13, SEQ ID NO: 14, or SEQ ID NO: 15. For example, variations of the probes and primers disclosed as SEQ ID NOs:3-12 can be made by "sliding" the probes and/or primers a few nucleotides 5' or 3' from their positions, and that such variation will still be specific for *S. pneumoniae* lytA, psaA, or ply.

Also provided by the present application are probes and primers that include variations to the nucleotide sequences shown in any of SEQ ID NOs:3-12, as long as such variations permit detection of the *S. pneumoniae* nucleic acid molecule. For example, a probe or primer can have at least 95% sequence identity such as at least 96%, at least 97%, at least 98%, at least 99% to a nucleic acid consisting of the sequence shown in any of SEQ ID NOs:3-12. In such examples, the number of nucleotides does not change, but the nucleic acid sequence shown in any of SEQ ID NOs:3-12 can vary at a few nucleotides, such as changes at 1, 2, 3, or 4 nucleotides.

The present application also provides probes and primers that are slightly longer or shorter than the nucleotide sequences shown in any of SEQ ID NOs:3-12, as long as such deletions or additions permit detection of the desired *S. pneumoniae* nucleic acid molecule, such as a *S. pneumoniae* lytA, psaA or ply sequence. For example, a probe can include a few nucleotide deletions or additions at the 5'- or 3'-end of the probe or primers shown in any of SEQ ID NOs:3-12, such as addition or deletion of 1, 2, 3, or 4 nucleotides from the 5'- or 3'-end, or combinations thereof (such as a deletion from one end and an addition to the other end). In such examples, the number of nucleotides changes.

Detection of *S. pneumoniae*

A major application of the *S. pneumoniae* specific primers and probes disclosed herein is for the detection of *S. pneumoniae* in a sample, such as a biological sample obtained from a subject that has or is suspected of having an *S. pneumoniae* infection. Thus, the disclosed methods can be used to diagnose if a subject has a *S. pneumoniae*. Accordingly, methods for the detection of *S. pneumoniae* nucleic acids are disclosed, for example to determine if a subject is infected with *S. pneumoniae*.

The methods described herein may be used for any purpose for which detection of *S. pneumoniae* is desirable, including diagnostic and prognostic applications, such as in laboratory and clinical settings. Appropriate samples include any conventional environmental or biological samples, including clinical samples obtained from a human or veterinary subject. Suitable samples include all biological samples useful for detection of bacterial infection in subjects, including, but not limited to, cells, tissues (for example, lung, liver and kidney), bone marrow aspirates, bodily fluids (for example, blood, serum, urine, cerebrospinal fluid, bronchoalveolar levage, tracheal aspirates, sputum, nasopharyngeal aspirates, oropharyngeal aspirates, saliva), eye swabs, cervical swabs, vaginal swabs, rectal swabs, stool, and stool suspensions. Other suitable samples include samples obtained from middle ear fluids, bronchoalveolar levage, tracheal aspirates, sputum, nasopharyngeal aspirates, oropharyngeal aspirates, or saliva. Standard techniques for acquisition of such samples are available. See for example, Schluger et al., *J. Exp. Med.* 176:1327-33 (1992); Bigby et al., *Am. Rev. Respir. Dis.* 133:515-18 (1986); Kovacs et al., *NEJM* 318:589-93 (1988); and Ognibene et al., *Am. Rev. Respir. Dis.* 129:929-32 (1984).

Detecting a *S. pneumoniae* nucleic acid in a sample involves contacting the sample with at least one of the *S. pneumoniae* specific probes disclosed herein that is capable of hybridizing to a *S. pneumoniae* nucleic acid, such as a *S. pneumoniae* lytA nucleic acid, *S. pneumoniae* psaA nucleic acid, or a *S. pneumoniae* ply nucleic acid, under conditions of very high stringency (such as a nucleic acid probe capable of hybridizing under very high stringency conditions to a *S. pneumoniae* nucleic acid sequence set forth as SEQ ID NO: 13, SEQ ID NO: 14, or SEQ ID NO: 15, for example a nucleic acid sequence at least 95% identical to the nucleotide sequence set forth as one of SEQ ID NO: 5, SEQ ID NO: 6, SEQ ID NO: 9, or SEQ ID NO: 12, such as a nucleic acid sequence consisting substantially of the nucleic acid sequence set forth as one of SEQ ID NO: 5, SEQ ID NO: 6, SEQ ID NO: 9, or SEQ ID NO: 12), and detecting hybridization between the *S. pneumoniae* nucleic acid and the probe. Detection of hybridization between the probe and the *S. pneumoniae* nucleic acid indicates the presence of the *S. pneumoniae* nucleic acid in the sample, for example detection of hybridization between the *S. pneumoniae* lytA probe and the *S. pneumoniae* lytA nucleic acid indicates the presence of the *S. pneumoniae* nucleic acid in the sample, detection of hybridization between the *S. pneumoniae* psaA probe and the *S. pneumoniae* psaA nucleic acid indicates the presence of the *S. pneumoniae* nucleic acid in the sample, and detection of hybridization between the *S. pneumoniae* ply probe and the *S. pneumoniae* ply nucleic acid indicates the presence of the *S. pneumoniae* nucleic acid in the sample.

In some embodiments, *S. pneumoniae* nucleic acids present in a sample are amplified prior to using a hybridization probe for detection. For instance, it can be advantageous to amplify a portion of the *S. pneumoniae* nucleic acid, and then detect the presence of the amplified *S. pneumoniae* nucleic acid. For example, to increase the number of nucleic acids that can be detected, thereby increasing the signal obtained. *S. pneumoniae* specific nucleic acid primers can be used to amplify a region that is at least about 50, at least about 60, at least about 70, at least about 80 at least about 90, at least about 100, at least about 200, or more base pairs in length to produce amplified *S. pneumoniae* specific nucleic acids.

Detecting the amplified product typically includes the use of labeled probes that are sufficiently complementary and hybridize to the amplified *S. pneumoniae* nucleic acid sequence. Thus, the presence, amount, and/or identity of the amplified product can be detected by hybridizing a labeled probe, such as a fluorescently labeled probe, complementary to the amplified product. In one embodiment, the detection of a target nucleic acid sequence of interest, such as a *S. pneumoniae* lytA nucleic acid, a *S. pneumoniae* psaA nucleic acid, or a *S. pneumoniae* ply nucleic acid, includes the combined use of PCR amplification and a labeled probe such that the product is measured using real-time PCR. In another embodiment, the detection of an amplified target nucleic acid sequence of interest includes the transfer of the amplified target nucleic acid to a solid support, such as a blot, for example a Northern blot, and probing the blot with a probe, for example a labeled probe, that is complementary to the amplified target nucleic acid sequence. In yet another embodiment, the detection of an amplified target nucleic acid sequence of interest includes the hybridization of a labeled amplified target nucleic acid to probes disclosed herein that are arrayed in a predetermined array with an addressable location and that are complementary to the amplified target nucleic acid.

Any nucleic acid amplification method can be used to detect the presence of *S. pneumoniae* in a sample. In one specific, non-limiting example, polymerase chain reaction (PCR) is used to amplify the *S. pneumoniae* nucleic acid sequences. In other specific, non-limiting examples, real-time PCR, reverse transcriptase-polymerase chain reaction (RT-PCR), real-time reverse transcriptase-polymerase chain reaction (rt RT-PCR), ligase chain reaction, or transcription-mediated amplification (TMA) is used to amplify the *S. pneumoniae* nucleic acid. In a specific example, the *S. pneumoniae* lytA nucleic acid is amplified by real-time PCR, for example real-time TAQMAN® PCR. Techniques for nucleic acid amplification are well-known to those of skill in the art.

Typically, at least two primers are utilized in the amplification reaction, Amplification of the *S. pneumoniae* nucleic acid involves contacting the *S. pneumoniae* nucleic acid with one or more primers that are capable of hybridizing to and directing the amplification of a *S. pneumoniae* nucleic acid (such as a primer capable of hybridizing under very high stringency conditions to a *S. pneumoniae* nucleic acid sequence set forth as SEQ NO:13, SEQ ID NO: 14, or SEQ ID NO: 15, for example a primer that is least 95% identical (such as 100% identical) to the nucleotide sequence set forth as one of SEQ ID NO: 3, SEQ ID NO: 4, SEQ ID NO: 7, SEQ ID NO: 8, SEQ ID NO: 10, or SEQ ID NO: 11).

In some embodiments, the sample is contacted with a pair of primers that include a forward and reverse primer that both hybridize to a *S. pneumoniae* lytA nucleic acid, such as a primer that is least 95% identical (such as 100% identical) to the nucleotide sequence set forth as SEQ ID NO: 3 and a primer that is least 95% identical (such as 100% identical) to the nucleotide sequence set forth as SEQ ID NO: 4. In some embodiments, the sample is contacted with a pair of primers that include a forward and reverse primer that both hybridize to a *S. pneumoniae* psaA nucleic acid, such as a primer that is least 95% identical (such as 100% identical) to the nucleotide sequence set forth as SEQ ID NO: 7 and a primer that is least 95% identical (such as 100% identical) to the nucleotide sequence set forth as SEQ ID NO: 8. In some embodiments, the sample is contacted with a pair of primers that include a forward and reverse primer that both hybridize to a *S. pneumoniae* ply nucleic acid, such as a primer that is least 95% identical (such as 100% identical) to the nucleotide sequence set forth as SEQ ID NO: 10 and a primer that is least 95% identical (such as 100% identical) to the nucleotide sequence set forth as SEQ ID NO: 11.

The amplified *S. pneumoniae* nucleic acid, can be detected in real-time, for example by real-time PCR, in order to determine the presence, and/or the amount of *S. pneumoniae* specific nucleic acid in a sample, such as *S. pneumoniae* lytA, psaA, or ply nucleic acid. In this manner, an amplified nucleic acid sequence, such as an amplified *S. pneumoniae* lytA, psaA, or ply nucleic acid sequence, can be detected using a probe specific for the product amplified from the *S. pneumoniae* sequence of interest, such as an amplified *S. pneumoniae* lytA, psaA, or ply nucleic acid sequence.

Real-time PCR monitors the fluorescence emitted during the reaction as an indicator of amplicon production during each PCR cycle as opposed to the endpoint detection. The real-time progress of the reaction can be viewed in some systems. Typically, real-time PCR uses the detection of a fluorescent reporter. Typically, the fluorescent reporter's signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed.

In one embodiment, the fluorescently-labeled probes rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a fluorophore and a non-fluorescent quencher on the same probe (for example, using a molecular beacon or a TAQMAN® probe) can identify a probe that specifically hybridizes to the DNA sequence of interest and in this way, using a *S. pneumoniae* lytA probe, a *S. pneumoniae* psaA probe, a *S. pneumoniae* ply probe, can detect the presence, and/or amount of *S. pneumoniae* in a sample. In some embodiments, the fluorescently-labeled DNA probes used to identify amplification products have spectrally distinct emission wavelengths, thus allowing them to be distinguished within the same reaction tube, for example in multiplex PCR, for example a multiplex real-time PCR. In some embodiments, the probes and primers disclosed herein are used in multiplex real-time PCR. For example, multiplex PCR permits the simultaneous detection of the amplification products of a lytA, psaA, and ply nucleic acid using the disclosed probes or even an other nucleic acid, such as a control nucleic acid, for example a RNAse P nucleic acid. Using the disclosed primers and probes, any combination of lytA, psaA, and ply can be detected.

In another embodiment, a melting curve analysis of the amplified target nucleic acid can be performed subsequent to the amplification process. The $T_m$ of a nucleic acid sequence depends on the length of the sequence and its G/C content. Thus, the identification of the $T_m$ for a nucleic acid sequence can be used to identify the amplified nucleic acid, for example by using double-stranded DNA binding dye chemistry, which quantitates the amplicon production by the use of a non-sequence specific fluorescent intercalating agent (such as SYBR-green or ethidium bromide). SYBR green is a fluorogenic minor groove binding dye that exhibits little fluorescence when in solution but emits a strong fluorescent signal upon binding to double-stranded DNA. Typically, SYBR green is used in singleplex reactions, however when coupled with melting point analysis, it can be used for multiplex reactions.

Any type of thermal cycler apparatus can be used for the amplification of the *S. pneumoniae* nucleic acid, such as a lytA, psaA, or ply nucleic acid and/or the determination of hybridization. Examples of suitable apparatuses include a PTC-100® Peltier Thermal Cycler (MJ Research, Inc.; San Francisco, Calif.), a ROBOCYCLER® 40 Temperature Cycler (Stratagene; La Jolla, Calif.), or a GENEAMP® PCR System 9700 (Applied Biosystems; Foster City, Calif.). For real-time PCR, any type of real-time thermocycler apparatus can be used. For example, a BioRad iCycler iQ™, LIGHT-CYCLER™ (Roche; Mannheim, Germany), a 7700 Sequence Detector (Perkin Elmer/Applied Biosystems; Foster City, Calif.), ABI™ systems such as the 7000, 7500, 7700, or 7900 systems (Applied Biosystems; Foster City, Calif.), or an MX4000™ MX3000™ or MX3005™ (Stratagene; La Jolla, Calif.); DNA Engine Opticon Continuous Fluorescence Detection System (MJ Research); and Cepheid SMARTCYCLER™ can by used to amplify nucleic acid sequences in real-time.

In some embodiments, detecting the presence of a *S. pneumoniae* nucleic acid sequence in a sample includes the extraction of *S. pneumoniae* DNA. DNA extraction relates to releasing DNA from a latent or inaccessible form in a cell or sample and allowing the DNA to become freely available. In such a state, it is suitable for effective detection and/or amplification of the *S. pneumoniae* nucleic acid. Releasing DNA may include steps that achieve the disruption of cells. Additionally, extraction of DNA may include steps that achieve at least a partial separation of the DNA dissolved in an aqueous medium from other cellular components, wherein such components may be either particulate or dissolved.

In some embodiments, detecting the presence of a *S. pneumoniae* lytA nucleic acid sequence in a sample includes the extraction of *S. pneumoniae* RNA. RNA extraction relates to releasing RNA from a latent or inaccessible form in a cell or sample and allowing the RNA to become freely available. In such a state, it is suitable for effective detection and/or amplification of the *S. pneumoniae* nucleic acid. Releasing RNA may include steps that achieve the disruption of cells. Extraction of RNA is generally carried out under conditions that effectively exclude or inhibit any ribonuclease activity that may be present. Additionally, extraction of RNA may include steps that achieve at least a partial separation of the RNA dissolved in an aqueous medium from other cellular components, wherein such components may be either particulate or dissolved.

One of ordinary skill in the art will know suitable methods for extracting nucleic acids such as RNA and/or DNA from a sample; such methods will depend upon, for example, the type of sample in which the *S. pneumoniae* nucleic acid is found. For example, the nucleic acids may be extracted using guanidinium isothiocyanate, such as the single-step isolation by acid guanidinium isothiocyanate-phenol-chloroform extraction of Chomczynski et al. (*Anal. Biochem.* 162:156-59, 1987). The sample can be used directly or can be processed, such as by adding solvents, preservatives, buffers, or other compounds or substances. Nucleic acids can be extracted using standard methods. For instance, rapid nucleic acid preparation can be performed using a commercially available kit (such as the QIAGEN® DNA Mini kit (QIAGEN®) Roche MagNA Pure Compact Nucleic Acid Isolation Kit I or RNEASY® Mini Kit (QIAGEN®); NUCLISENS® NASBA Diagnostics (bioMérieux); or the MASTERPURE™ Complete DNA and RNA Purification Kit (EPICENTRE)).

In some embodiments, the probe is detectably labeled, either with an isotopic or non-isotopic label; in alternative embodiments, the *S. pneumoniae* nucleic acid is labeled. Non-isotopic labels can, for instance, comprise a fluorescent or luminescent molecule, or an enzyme, co-factor, enzyme substrate, or hapten. The probe is incubated with a single-stranded or double-stranded preparation of RNA, DNA, or a mixture of both, and hybridization determined. In some examples, the hybridization results in a detectable change in signal such as in increase or decrease in signal, for example from the labeled probe. Thus, detecting hybridization comprises detecting a change in signal from the labeled probe during or after hybridization relative to signal from the label before hybridization.

*Streptococcus pneumoniae* Identification Arrays

An array containing a plurality of heterogeneous probes for the detection, of *S. pneumoniae* are disclosed. Such arrays may be used to rapidly detect *S. pneumoniae* in a sample.

Arrays are arrangements of addressable locations on a substrate, with each address containing a nucleic acid, such as a probe, such as a *S. pneumoniae* lytA psaA, or ply probe as disclosed herein. In some embodiments, each address corresponds to a single type or class of nucleic acid, such as a single probe, though a particular nucleic acid may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

In some embodiments, a *S. pneumoniae* detection array is a collection of separate probes at the array addresses. The *S. pneumoniae* detection array is then contacted with a sample suspected of containing *S. pneumoniae* nucleic acids under conditions allowing hybridization between the probe and nucleic acids in the sample to occur. Any sample potentially containing, or even suspected of containing, *S. pneumoniae* nucleic acids may be used, including nucleic acid extracts, such as amplified or non-amplified DNA or RNA preparations. A hybridization signal from an individual address on the array indicates that the probe hybridizes to a nucleotide within the sample. This system permits the simultaneous analysis of a sample by plural probes and yields information identifying the *S. pneumoniae* nucleic acids contained within the sample. In alternative embodiments, the array contains *S. pneumoniae* nucleic acids and the array is contacted with a sample containing a probe. In any such embodiment, either the probe or the *S. pneumoniae* nucleic acids may be labeled to facilitate detection of hybridization.

The nucleic acids may be added to an array substrate in dry or liquid form. Other compounds or substances may be added to the array as well, such as buffers, stabilizers, reagents for detecting hybridization signal, emulsifying agents, or preservatives.

In certain examples, the array includes one or more molecules or samples occurring on the array a plurality of times (twice or more) to provide an added feature to the array, such as redundant activity or to provide internal controls.

Within an array, each arrayed nucleic acid is addressable, such that its location may be reliably and consistently determined within the at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (for example, in radially distributed lines, a "spokes and wheel" pattern, or ordered clusters). Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

An address within the array may be of any suitable shape and size. In some embodiments, the nucleic acids are suspended in a liquid medium and contained within square or rectangular wells on the array substrate. However, the nucleic acids may be contained in regions that are essentially triangular, oval, circular, or irregular. The overall shape of the array itself also may vary, though in some embodiments it is substantially flat and rectangular or square in shape.

S. pneumoniae detection arrays may vary in structure, composition, and intended functionality, and may be based on either a macroarray or a macroarray format, or a combination thereof. Such arrays can include, for example, at least 10, at least 25, at least 50, at least 100, or more addresses, usually with a single type of nucleic acid at each address. In the case of macroarrays, sophisticated equipment is usually not required to detect a hybridization signal on the array, though quantification may be assisted by standard scanning and/or quantification techniques and equipment. Thus, macroarray analysis as described herein can be carried out in most hospitals, agricultural and medial research laboratories, universities, or other institutions without the need for investment in specialized and expensive reading equipment.

Examples of substrates for the arrays disclosed herein include glass (e.g., functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (for example glass or a supported membrane) or flexible (such as a polymer membrane). One commercially available product line suitable for probe arrays described herein is the Microlite line of MICROTITER® plates available from Dynex Technologies UK (Middlesex, United Kingdom), such as the Microlite 1+96-well plate, or the 384 Microlite+384-well plate.

Addresses on the array should be discrete, in that hybridization signals from individual addresses can be distinguished from signals of neighboring addresses, either by the naked eye (macroarrays) or by scanning or reading by a piece of equipment or with the assistance of a microscope (microarrays).

Addresses in an array may be of a relatively large size, such as large enough to permit detection of a hybridization signal without the assistance of a microscope or other equipment. Thus, addresses may be as small as about 0.1 mm across, with a separation of about the same distance. Alternatively, addresses may be about 0.5, 1, 2, 3, 5, 7, or 10 mm across, with a separation of a similar or different distance. Larger addresses (larger than 10 mm across) are employed in certain embodiments. The overall size of the array is generally correlated with size of the addresses (for example, larger addresses will usually be found on larger arrays, while smaller addresses may be found on smaller arrays). Such a correlation is not necessary, however.

The arrays herein may be described by their densities (the number of addresses in a certain specified surface area). For macroarrays, array density may be about one address per square decimeter (or one address in a 10 cm by 10 cm region of the array substrate) to about 50 addresses per square centimeter (50 targets within a 1 cm by 1 cm region of the substrate). For microarrays, array density will usually be one or more addresses per square centimeter, for instance, about 50, about 100, about 200, about 300, about 400, about 500, about 1000, about 1500, about 2,500, or more addresses per square centimeter.

The use of the term "array" includes the arrays found in DNA microchip technology. As one, non-limiting example, the probes could be contained on a DNA microchip similar to the GENECHIP® products and related products commercially available from Affymetrix, Inc. (Santa Clara, Calif.). Briefly, a DNA microchip is a miniaturized, high-density array of probes on a glass wafer substrate. Particular probes are selected, and photolithographic masks are designed for use in a process based on solid-phase chemical synthesis and photolithographic fabrication techniques similar to those used in the semiconductor industry. The masks are used to isolate chip exposure sites, and probes are chemically synthesized at these sites, with each probe in an identified location within the array. After fabrication, the array is ready for hybridization. The probe or the nucleic acid within the sample may be labeled, such as with a fluorescent label and, after hybridization, the hybridization signals may be detected and analyzed.

Kits

The nucleic acid primers and probes disclosed herein can be supplied in the form of a kit for use in the detection S. pneumoniae, including kits for any of the arrays described above. In such a kit, an appropriate amount of one or more of the nucleic acid probes and/or primers (such as S. pneumoniae lytA psaA, or ply probes and primers as disclosed herein) is provided in one or more containers or held on a substrate. A nucleic acid probe and/or primer may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. The kits can include either labeled or unlabeled nucleic acid probes for use in detection of S. pneumoniae nucleotide sequences.

In some applications, one or more primers (as described above), such as pairs of primers, may be provided in pre-measured single use amounts in individual, typically disposable, tubes or equivalent containers. With such an arrangement, the sample to be tested for the presence of S. pneumoniae nucleic acids can be added to the individual tubes and amplification carried out directly.

The amount of nucleic acid primer supplied in the kit can be any appropriate amount, and may depend on the target market to which the product is directed. For instance, if the kit is adapted for research or clinical use, the amount of each nucleic acid primer provided would likely be an amount sufficient to prime several PCR amplification reactions. General guidelines for determining appropriate amounts may be found in Innis et al., Sambrook et al., and Ausubel et al. A kit may include more than two primers in order to facilitate the PCR amplification of a larger number of S. pneumoniae nucleotide sequences.

In some embodiments, kits also may include the reagents necessary to carry out PCR amplification reactions, including DNA sample preparation reagents, appropriate buffers (such as polymerase buffer), salts (for example, magnesium chloride), and deoxyribonucleotides (dNTPs).

One or more control sequences for use in the PCR reactions also may be supplied in the kit (for example, for the detection of human RNAse P).

Particular embodiments include a kit for detecting a S. pneumoniae nucleic acid based on the arrays described above. Such a kit includes at least one probe specific for a S. pneumoniae nucleic acid (as described above) and instructions. A kit may contain more than one different probe, such as 2, 3, 4, 5, 6, 7, 8, 9, 10, 11, 12, 13, 14, 15, 20, 25, 50, 100, or more probes. The instructions may include directions for obtaining a sample, processing the sample, preparing the probes, and/or contacting each probe with an aliquot of the sample. In certain embodiments, the kit includes an apparatus for separating the different probes, such as individual containers (for example, microtubules) or an array substrate (such as, a 96-well or 384-well microtiter plate). In particular embodiments, the kit includes prepackaged probes, such as probes suspended in suitable medium in individual containers (for example, individually sealed EPPENDORF® tubes) or the wells of an array substrate (for example, a 96-well microtiter plate sealed with a protective plastic film). In other particular embodiments, the kit includes equipment, reagents, and instructions for extracting and/or purifying nucleotides from a sample.

Synthesis of Oligonucleotide Primers and Probes

In vitro methods for the synthesis of oligonucleotides are well known to those of ordinary skill in the art; such methods can be used to produce primers and probes for the disclosed methods. The most common method for in vitro oligonucleotide synthesis is the phosphoramidite method, formulated by Letsinger and further developed by Caruthers (Caruthers et al., Chemical synthesis of deoxyoligonucleotides, in Methods Enzymol. 154:287-313, 1987). This is a non-aqueous, solid phase reaction carried out in a stepwise manner, wherein a single nucleotide (or modified nucleotide) is added to a growing oligonucleotide. The individual nucleotides are added in the form of reactive 3'-phosphoramidite derivatives. See also, Gait (Ed.), Oligonucleotide Synthesis. A practical approach, IRL Press, 1984.

In general, the synthesis reactions proceed as follows: A dimethoxytrityl or equivalent protecting group at the 5' end of the growing oligonucleotide chain is removed by acid treatment. (The growing chain is anchored by its 3' end to a solid support such as a silicon bead.) The newly liberated 5' end of the oligonucleotide chain is coupled to the 3'-phosphoramidite derivative of the next deoxynucleotide to be added to the chain, using the coupling agent tetrazole. The coupling reaction usually proceeds at an efficiency of approximately 99%; any remaining unreacted 5' ends are capped by acetylation so as to block extension in subsequent couplings. Finally, the phosphite triester group produced by the coupling step is oxidized to the phosphotriester, yielding a chain that has been lengthened by one nucleotide residue. This process is repeated, adding one residue per cycle. See, for example, U.S. Pat. Nos. 4,415,732, 4,458,066, 4,500,707, 4,973,679, and 5,132,418. Oligonucleotide synthesizers that employ this or similar methods are available commercially (for example, the PolyPlex oligonucleotide synthesizer from Gene Machines, San Carlos, Calif.). In addition, many companies will perform such synthesis (for example, Sigma-Genosys, The Woodlands, Tex.; Qiagen Operon, Alameda, Calif.; Integrated DNA Technologies, Coralville, Iowa; and TriLink Bio-Technologies, San Diego, Calif.).

The following examples are provided to illustrate particular features of certain embodiments. However, the particular features described below should not be construed as limitations on the scope of the invention, but rather as examples from which equivalents will be recognized by those of ordinary skill in the art.

EXAMPLES

Example 1

Materials and Methods

This example describes the materials and methods used to determine the specificity and sensitivity of the disclosed probes and primers.

Bacterial Isolates

The disclosed probes and primers where tested for specificity for S. pneumoniae using a panel that included 67 S. pneumoniae strains representing 44 different S. pneumoniae serotypes (1, 2, 4, 5, 6A, 6B, 7B, 7C, 7F, 8, 9N, 9V, 10A, 11A, 12F, 13, 14, 15B, 15A, 15C, 16F, 17A, 17F, 18B, 18C, 18F, 19A, 19C, 19F, 20, 21, 22A, 22F, 23B, 23F, 24A, 24B, 28A, 28F, 32F, 33A, 33F, 35A, 35F, 40, and 3 non-capsulated from conjunctivitis outbreaks) and 104 non-pneumococcal isolates including S. pseudopneumoniae, S. mitis, S. oxalis, S. sanguinis, S. parasanguinis, S. peroris, S. infantis, S. gordonii, S. cristatus, S. salivarius, S. vestibularis, S. australis, S. sinensis, S. oligofermentans, S. intestinalis, S. pyogenes, S. agalactiae, S. canis, S. anginosus, S. equi subsp. equi, S. equi subsp. zooepidemicus, S. porcinus, S. dysgalactiae, S. constellatus, S. iniae, S. intermedius, S. aureus, S. warneri, 13 viridans streptococci not identified to the species level, Dolostigranulum pigrum, Enterococcus faecalis, Escherichia coli, Chlamydia pneumoniae, C. psittaci, Mycoplasma pneumoniae, Legionella pneumophila, Haemophilus influenzae types a-f and NT, H. parainfluenzae, Corynebacterium diphtheriae, C. pseudotuberculosis, Nocardia farcinica, N. asteroides, Klebsiella pneumoniae, Mycobaterium fortuitum, M. tuberculosis, Pseudomonas aeruginosa, Bordetella pertussis and B. bronchiseptica.

S. pneumoniae ATCC strain 33400 was used as a positive control in all assays described below. All bacteria isolates were obtained from the culture collections of CDC laboratories (Streptococcus Laboratory, Respiratory Diseases Branch and Molecular Sequencing Laboratory, Meningitis and Vaccine Preventable Diseases Branch).

Optochin Susceptibility Test (OPT)

OPT susceptibility testing was performed on 5% sheep blood agar plates at 5% $CO_2$ environments as described in Arbique et al. (Arbique et al., J. Clin. Microbiol. 42: 4686-4696, 2004, which is incorporated herein by reference to the extent that it discloses this test).

Bile Solubility (BS) Test

The tube BS test was performed as previously described (Arbique et al., J. Clin. Microbiol. 42: 4686-4696, 2004, and Ruoff et al., Streptococcus p. 405-421. In P. R. Murray et al. (ed.), Manual of clinical microbiology 8th ed. American Society for Microbiology, Washington, D.C, 2003, both of which is incorporated herein by reference to the extent that they discloses this test).

DNA Probe Hybridization Test

The ACCUPROBE® Streptococcus pneumoniae culture identification test, based on the rRNA gene sequence, was performed according to the manufacturer's instructions (Gen-Probe, San Diego, Calif.).

DNA-DNA Reassociation

Growth, harvesting and lysis of the bacterial cells were performed as described previously (Arbique et al., J. Clin. Microbiol. 42: 4686-4696, 2004, and Brenner et al., J. Clin. Microbiol. 15:1133-1140, 1982). Extraction and purification of DNA and DNA-DNA reassociation studies including determination of DNA relatedness by the hydroxyapatite hybridization method were performed as described by Brenner and colleagues (Brenner et al., J. Clin. Microbiol. 15:1133-1140, 1982). DNA hybridization experiments were performed at 55° C. for optimal DNA reassociation and at the stringent DNA reassociation temperature of 70° C. The levels of divergence within related sequences were determined by assuming that each degree of heteroduplex instability was caused by 1% unpaired bases. Divergence, expressed by the change in melting temperature, is the decrease in the thermal stability (in degrees Celsius) of the heterologous DNA duplex relative to that of the homologous duplexes. Divergence was calculated to the nearest 0.5%.

Clinical Specimens

Clinical specimens included serum, middle ear fluids (MEFs), and cerebral spinal fluids (CSFs) and were obtained in accordance with CDC Institutional Review Board (IRB) stipulations. The sera and MEFs were obtained from the Soroka University Hospital in Beer-Sheva, Israel. Serum specimens were collected from 15 patients with pneumococcal bacteremia and 15 age-matched, ethnic group-matched, healthy control children in whom nasopharyngeal (NP) culture was negative for S. pneumoniae. MEF specimens consisted of 10 S. pneumoniae culture positive middle ear fluids and 10 S. pneumoniae culture negative but H. influenzae positive MEFs. Twenty-five CSFs were obtained from the Laboratorio Central do Estado do Rio Grande do Sul, Porto Alegre, Brasil and consisted of 15 specimens from meningitis patients that were pneumococcal culture positive and 10 CSFs from pneumococcal negative, N. meningitidis positive patients. Specimens were shipped on dry ice and frozen at −70° C. upon arrival.

DNA Extraction for Real-Time PCR Analysis

DNA was extracted from the isolates by a modification of the QIAGEN® DNA Mini kit (QIAGEN® Inc., Valencia, Calif.) method. Briefly, a loopfull of overnight growth from a blood agar plate was resuspended in lysis buffer (20 mM Tris-HCL pH 8.0, 2.0 mM EDTA, 1.2% Triton X100 containing 0.04 g/ml lysozyme and 75 U/ml of mutanolysin (Sigma Chemical Co, St Louis, Mo.) and incubated for one hour at 37° C. in a water-bath. The remaining procedures followed the manufacture's recommendations.

For clinical specimens, 200 µl of clinical material was added to 100 µl of TE buffer containing 0.04 g/ml lysozyme and 75 U/ml of mutanolysin (Sigma Chemical Co) and incubated for one hour in a 37° C. water bath. All subsequent steps were as outlined in the QIAGEN® DNA mini protocol booklet. DNA was eluted in 100 µl of QIAGEN® EA elution buffer and stored at −20° C. Concentrations of extracted DNA from bacterial cultures were determined by NANODROP® (NANODROP® Technologies, Wilmington, Del.).

Real-Time PCRs for lytA, ply and psaA

The two previously published real-time PCR assays were performed as described (Corless et al., J. Clin. Microbiol. 39:1553-1558, 2001; McAvin et al., J. Clin. Microbiol. 39:3446-3451, 2001).

For development of the assays disclosed herein, oligonucleotide primers and fluorescent dye-labeled probes were designed based on previously published lytA, ply, and psaA gene sequences and sequences available in GENBANK® using the PRIMER EXPRESS® Software (Applied Biosystems, AB, Foster City, Calif.). The probes were labeled 5' with either 6-carboxy-fluorescein (FAM) or in the case of the psaA probe with hexachloro-6-carboxy-fluorescein (HEX). Black hole quencher (BHQ1®, Biosearch Technologies, Novato, Calif.) was either placed at the 3' end of the probe or internally on a thymidine (Table 1). If internally quenched the 3' end was capped with a phosphate group to prevent extension of the probe. Primer and probe sequences are listed in Table 1.

TABLE 1

Real-time PCR primers and probes

| Oligonucleotide | Sequence | Nucleotide position | Accession number |
|---|---|---|---|
| lytA-CDC forward | 5'-ACGCAATCTAGCAGATGAAGCA-3' (SEQ ID NO: 3) | 1841014 | AE005672 |
| lytA-CDC reverse | 5'-TCGTGCGTTTTAATTCCAGCT-3' (SEQ ID NO: 4) | 1840961 | |
| lytA-CDC_1 probe | 5'-FAM GCCGAAAACGCTTGATACAGGGAG-3' BHQ1 (SEQ ID NO: 5) | 1840985 | |
| lytA-CDC_2 probe | 5'-FAM TGCCGAAAACGCTTGATACAGGGAG-3' BHQ1 (SEQ ID NO: 6) | 1840984 | |
| psaA-CDC forward | 5'-GCCCTAATAAATTGGAGGATCTAATGA-3' (SEQ ID NO: 7) | 166 | U53509 |
| psaA-CDC reverse | 5'-GACCAGAAGTTGTATCTTTTTTCCG-3' (SEQ ID NO: 8) | 279 | |
| psaA-CDC probe[a,b] | 5'-HEX CTAGCACATGCTACAAGAATGATTGC AGAAAGAAA-3' phosphate (SEQ ID NO: 9) | 219 | |
| ply-CDC forward | 5'-GCTTATGGGCGCCAAGTCTA -3' (SEQ ID NO: 10) | 721 | AE008539 |
| ply-CDC reverse | 5'-CAAAGCTTCAAAAGCAGCCTC TA-3' (SEQ ID NO: 11) | 798 | |
| ply-CDC probe[b,c] | 5'-FAM CTCAAGTTGGAAACCACGAGTAAGA GTGATGAA-3' phosphate (SEQ ID NO: 12) | 742 | |

[a] psaA probe is designed to bind to the reverse strand of the amplicon
[b] T indicates the thymidine on which the internal BHQ quencher was attached
[c] For multiplex detection the 5'end label was changed to CAL Flour 61

Assays were carried out in a final 25 µl reaction volume, using the TAQMAN®Universal Master Mix kit (AB) according to instructions with 2.5 µl of sample DNA. Primer and probe concentrations for each of the three assays were optimized; and in accordance with the experimentally optimized concentrations, 500, 200, 200 nM of psaA-CDC, lytA-CDC, ply-CDC primers and 100, 200, 200 nM of psaA-CDC, lytA-CDC, ply-CDC probes, respectively, were used for subsequent experiments. A no-template control and a *Streptococcus pneumoniae* positive DNA control (*S. pneumoniae* ATCC 33400) were included in every run. DNA was amplified with Mx3000P (Stratagene, La Jolla, Calif.) or 7500 Real-time PCR system (AB), using the following cycling parameters: 95° C. for 10 min followed by 40 cycles of 95° C. for 15 s and 60° C. for 1 min. Amplification data were analyzed by instrument software (STRATAGENE® or Applied Biosystems). Negative samples were defined as those with cycle thresholds greater than >40. New assays are designated lytA-CDC, ply-CDC, and psaA-CDC.

Real-Time PCR Analytical Sensitivity and Specificity Determinations

For lower limit of detection (LLD) assessments, serial 10-fold dilutions (equivalent to 6666 to 6.6 copies) of purified DNA from the pneumococcal reference strain ATCC 33400 were prepared and aliquots tested using all five real-time PCR protocols. Specificity determinations were made by testing extracted DNAs at 5 ng/ul from 67 *S. pneumoniae* isolates and 104 non pneumococcal isolates (listed above) in all five assays.

Real-Time PCR of Clinical Samples

*S. pneumoniae* DNA detection in serum, MEFs and CSFs were performed in parallel on aliquots of the same specimen for all assays. Extracted DNA (2.50 µl of undiluted or 2.5 µl of 1:3 dilution) from serum, MEFs or CSF was used in amplification reactions. All assays of each clinical sample were performed in triplicate. A specimen was considered positive if two of the three triplicates gave a positive result within the <40 cycle cut-off. Assay protocols were as described above. An RNaseP human gene control reaction was performed independently on each sample to check for the presence of inhibitors. Failure to get amplification in this reaction was considered indicative of inhibitors.

Mutiplex Real-Time PCRs for psaA-CDC, lytA-CDC and ply-CDC

The three sets of primers and probes were combined into a single reaction mixture for multiplex detection. Modifications to the single gene detection assays included: use of QIAGEN's® QUANTITECT® Multiplex PCR NoROX master mix, changing the ply-CDC gene probe fluorescent label from FAM to 5' CAL FLOUR RED 610®, 3' BHQ2® (Biosearch Technologies) and reduction of the concentration of the lytA FAM probe to 100 nM from the original to 200 nM. Temperatures and number of cycles remained the same as described in the original single PCR protocols.

Example 2

Lower Limit of Detection of Assays for *Streptococcus pneumoniae* Detection

This example describes the methodology employed to determine the sensitivity of the disclosed probes and primers and methods of using such probes and primers versus the probe and primer sets described by Corless et al. and McAvin et al.

The analytical lower limit of detection (LLD) for the five assays were measured by amplifying serial dilutions of purified extracted genomic DNA from the positive control strain *Streptococcus pneumoniae* ATCC 33400. All five assays showed a high sensitivity with their respective primer pairs and probes with a limit of detection equivalent to <10 copies, except for the psaA-CDC that was approximately 2 fold less sensitive. All standard curves generated had slopes of −3.4 to −3.2 with $R^2$>0.96. Efficiencies of the assays were very similar ranging from 96% to 100%. Evaluation of the five assays for their ability to amplify DNA from a panel of 67 *S. pneumoniae* strains representing 45 serotypes and non-typeable *S. pneumoniae* resulted in 100% amplification or detection of DNA from all *S. pneumoniae* strains tested.

Example 3

Specificity of Assays for *Streptococcus pneumoniae* Detection

This example describes the methodology employed to determine the specificity of the disclosed probes and primers and methods of using such probes and primers versus the probe and primer sets described by Corless et al. and McAvin et al.

The analytical specificity of each of the five assays was evaluated and compared by amplifying extracted DNA from 104 strains of non-pneumococcal bacteria. These strains represented several genera of gram-positive and gram-negative bacteria some of which inhabit the oral cavity. No amplification occurred with any of the non streptococci in the specificity panel. There was however amplification with some strains of P-LVS and Spseudo. The P-LVS were specifically selected from among strains that were submitted to the *Streptococcus* Laboratory, which had been difficult to identify or classify using the standard methodology criteria. DNA/DNA reassociation analysis had been performed on these isolates in addition to BS, OPT, and ACCUPROBE®. DNA/DNA reassociation values revealed that these P-LVS and the Spseudo (Table 2) were not *S. pneumoniae*.

TABLE 2

| | DNA-DNA hybridization and real-time PCR for un-identified viridans streptococci and *Streptococcus pseudopneumoniae* | | | | | | | | | | | | |
|---|---|---|---|---|---|---|---|---|---|---|---|---|---|
| | Identification test | | | | | Reference strains DNA labeled: *S. pneumoniae* ATCC 33400[T]/ *S. pseudopneumoniae* ATCC BAA 960[T] | | | Real-time PCR | | | | |
| Strains | Geographic Origin | Specimen | OPT | BS | GP | RBR at 55° C. | RBR at 70° C. | D | psaA-CDC | lytA-McAvin | lytA-CDC | ply-Corless | ply-CDC |
| *S. pneumoniae* | | | | | | | | | | | | | |
| ATCC 33400[T] Un-identified | | S | + | + | | 100/55 | 100/28 | 0.0/3.5 | + | + | + | + | + |

TABLE 2-continued

DNA-DNA hybridization and real-time PCR for un-identified viridans streptococci and *Streptococcus pseudopneumoniae*

| | Identification test | | | | | Reference strains DNA labeled: S. pneumoniae ATCC 33400[T]/ S. pseudopneumoniae ATCC BAA 960[T] | | | Real-time PCR | | | | |
|---|---|---|---|---|---|---|---|---|---|---|---|---|---|
| Strains | Geographic Origin | Specimen | OPT | BS | GP | RBR at 55° C. | RBR at 70° C. | D | psaA-CDC | lytA-McAvin | lytA-CDC | ply-Corless | ply-CDC |
| viridans streptococci | | | | | | | | | | | | | |
| 868-84 | MD | blood | R | − | − | 66/nd | 59/nd | 4.5/nd | − | − | − | + | + |
| 2901-90 | AL | throat | R | + | − | 65/nd | 51/nd | 6.0/nd | − | − | − | + | + |
| 2904-90 | AL | throat | S | + | − | 61/nd | 49/nd | 5.5/nd | − | − | − | + | − |
| 2909-90 | AL | throat | R | − | − | 61/nd | 46/nd | 6.0/nd | − | − | − | + | + |
| 2913-90 | AL | throat | S | − | − | 65/52 | 58/44 | 4.5/4.5 | − | − | − | + | + |
| 2916-90 | AL | throat | R | − | − | 58/nd | 42/nd | 6.0/nd | − | − | − | + | + |
| 2918-90 | AL | throat | S | + | − | 63/nd | 54/nd | 6.0/nd | − | − | − | + | + |
| 2919-90 | AL | throat | R | − | − | 63/nd | 54/nd | 4.5/nd | − | − | − | + | − |
| 2920-90 | AL | throat | S | + | − | 62/nd | 53/nd | 6.5/nd | − | − | − | + | + |
| 2921-90 | AL | throat | R | − | − | 62/nd | 58/nd | 4.5/nd | − | − | − | + | − |
| 2939-90 | AL | throat | R | − | − | 66/nd | 57/nd | 4.0/nd | − | − | − | + | + |
| S. pseudopneumoniae | | | | | | | | | | | | | |
| ATCC BAA-960[T] | NS-CA | sputum | R | − | + | 62/100 | 56/100 | 4.0/0.0 | − | − | − | + | + |
| 253-03 | NS-CA | sputum | R | − | + | 70/84 | 60/74 | 4.0/2.0 | − | − | − | + | + |
| 276-03 | NS-CA | sputum | R | − | + | 68/83 | 53/77 | 4.0/1.0 | − | − | − | + | + |
| 288-03 | NS-CA | sputum | R | − | + | 70/82 | 57/50 | 4.0/0.5 | + | + | − | + | + |
| 290-03 | NS-CA | sputum | R | − | + | 70/81 | 64/75 | 4.0/1.5 | − | − | − | + | + |
| 2482-91 | AL | throat | R | − | + | 58/72 | 46/71 | 3.0/1.0 | − | − | − | + | + |
| 2483-91 | AL | throat | R | − | + | 58/76 | 46/71 | 3.5/1.5 | − | − | − | + | + |
| 2497-91 | AL | throat | R | − | + | 37/82 | 49/80 | 3.5/2.0 | + | − | − | + | + |
| 2946-98 | AL | throat | R | − | + | 61/76 | 54/76 | 3.0/1.5 | − | + | − | + | + |
| 2987-98 | AZ | NP swab | R | − | + | 61/98 | 50/73 | 3.0/1.0 | − | + | − | + | + |

[T], type strain; OPT, susceptibility to optochin; BS, bile solubility; GP, GenProbe Accuprobe Pneumococcus culture identification test; RBR relative binding relation, at 55° C. (optimal temperature) at 70° C. (stringent temperature); D, divergence calculated to the nearest 0.5%; nd, not done; AL, Alaska; AZ, Arizona; MD, Maryland; NS-CA, Nova Scotia-Canada;

Analysis of these strains using real-time PCR demonstrated that the new lytA-CDC real-time PCR assay was the most specific (100%), showing no detectable fluorescent signal with DNA from non-*S. pneumoniae* organisms in the specificity panel (Table 2). This was followed by psaA-CDC real-time PCR (98%), which gave positive results with two of the Spseudo and the lytA-McAvin real-time PCR (96%) published by McAvin et al. which was positive for four Spseudo. No amplification occurred with DNAs from P-LVS with lytA-McAvin, lytA-CDC and psaA-CDC primer probe sets (Table 2). The two assays for the ply *S. pneumoniae* gene gave positive reactions with all Spseudo; of the other P-LVS, positive reactions occurred with both ply (13 of 13) and ply-CDC (10 of 13) assays, making final specificities 78% and 81% respectively.

Both the lytA-CDC and the psaA-CDC real-time PCR were highly specific, showing no amplification with P-LVS isolates. The psaA-CDC real-time PCR was slightly less specific, amplifying two of the Spseudo. These results correlate with an earlier study using conventional PCR, showing the utility of these genes in discriminating *S. pneumoniae*.

Example 4

Detection of *Streptococcus pneumoniae* in Clinical Samples

This example describes the detection of *S. pneumoniae* in clinical samples using the disclosed probes and primers and methods of using such probes and primers versus the probe and primer sets described by Corless et al. and McAvin et al.

The five assays were used on three types of clinical specimens (described above) to evaluate and compare assays (Table 3).

TABLE 3

Assay results for clinical specimens for all five real-time PCRs.

| | | | Real-time-PCR | | | | | | | | |
|---|---|---|---|---|---|---|---|---|---|---|---|
| | | | psaA-CDC | | lytA-McAvin | | lytA-CDC | | ply-CDC | | ply-Corless | |
| Specimens[a] | S. pneumoniae Culture | N. | (+) | (−) | (+) | (−) | (+) | (−) | (+) | (−) | (+) | (−) |
| Serum | + | 15[b] | 7 | 8 | 7 | 8 | 8[c] | 7 | 8[c] | 7 | 6 | 9 |
|  | − | 15 | 0 | 15 | 0 | 15 | 1[c] | 14 | 1[c] | 14 | 0 | 15 |
| MEF | + | 10 | 10 | 0 | 10 | 0 | 10 | 0 | 10 | 0 | 10 | 0 |
|  | − | 10 | 6 | 4 | 6 | 4 | 6 | 4 | 7[c] | 3 | 6 | 4 |

TABLE 3-continued

Assay results for clinical specimens for all five real-time PCRs.

| Specimens[a] | S. pneumoniae Culture | N. | Real-time-PCR | | | | | | | | | |
|---|---|---|---|---|---|---|---|---|---|---|---|---|
| | | | psaA-CDC | | lytA-McAvin | | lytA-CDC | | ply-CDC | | ply-Corless | |
| | | | (+) | (−) | (+) | (−) | (+) | (−) | (+) | (−) | (+) | (−) |
| CSF | + | 15 | 15 | 0 | 15 | 0 | 15 | 0 | 15 | 0 | 15 | 0 |
| | − | 10 | 1[d] | 9 | 2[c,d] | 8 | 3[c,d] | 7 | 2[c,d] | 8 | 2[d] | 8 |

[a]MEF, middle ear fluids; CSF, cerebral spinal fluids
[b]One serum was RNase P gene negative
[c]Average of Ct values = ≦38 for lytA-McAvin, lytA-CDC, ply-CDC
[d]Ct values ≦37 for all 5 PCR tested for that one specimen All five assays showed excellent correlation. When specimens were positive or negative in one assay, identical specimens were generally positive or negative in the other assays. Differences were only in total numbers positive or negative for each. Sensitivities were calculated based on the 15 culture positive serum specimens even though one of these was RNase P negative, indicating inhibition. Sensitivities with serum samples were 53% (8/15) for lytA-CDC and ply-CDC (1 additional positive for each but different specimens), 47% (7/15) for lytA and psaA, and 40% (6/15) for *S. pneumoniae* ply. Analysis of the *S. pneumoniae* culture negative sera showed good correlation between the assays as well as good specificities. No positives occurred for psaA, lytA and ply, resulting in a 100% specificity with serum.

Analysis of MEFs and CSFs revealed that all five assays gave positive results for all 10 of the Spn-positive MEFs and all 15 CSFs, yielding sensitivities of 100%. Specificity evaluations of the 10 culture negative MEFs resulted in positives with the same six MEF specimens for psaA-CDC, lytA-McAvin, lytA-CDC, and ply-Corless real-time PCR assays yielding 40% specificities. An additional specimen was positive by ply-CDC for a 30% specificity. Examination of *Streptococcus pneumoniae*-negative CSFs showed good specificity. Positives were 1 of 10 (90% specificity) for psaA, 2 of 10 (80% specificity) for lytA-McAvin, ply-CDC, ply-Corless and 3 of 10 (70% specificity) for lytA-CDC.

Example 5

Mutiplex CDC Real-Time PCRs for psaA, lytA, and ply

This example describes the detection of *S. pneumoniae* using the disclosed probes and primers in a multiplex real-time PCR assay.

To ascertain if combining the primer probe sets to detect all three genes at once would be advantageous in improving sensitivity we constructed a multiplex of the three newly developed assays. LLD evaluations with serial dilutions of known concentrations of the pneumococcal positive control ATCC 33400 were done and results compared to the singleplex assay for each gene. These studies showed that variation was less than ±1 $C_t$ value (cycle number where the fluorescence value crosses the threshold) when compared to all the singleplex PCR's. Evaluation of the Spseudo and other P-LVS bacteria yielded results similar to the individual assays. There were no additional positive or negative reactions.

Currently, the trend is to multiplex assays for simultaneous detection of various pathogens, representing a savings in time and money. We have done this for a single pathogen but would propose that our lytA-CDC or psaA-CDC primer probe sets would provide high specificity in a respiratory platform multiplexed with primers and probes for detection of other respiratory pathogens. This potential for multiplexing and the speed of performance make these assays promising tools for molecular detection and epidemiologic carriage studies. The use of this technology should offer an added advantage when used in conjunction with other assays for pneumococcal disease diagnosis.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, chemical moieties, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims.

We claim:

1. A method for detecting a *Streptococcus pneumoniae* nucleic acid in a sample, comprising:
   contacting the sample with at least one probe capable of hybridizing under very high stringency conditions to a *Streptococcus pneumoniae* nucleic acid sequence set forth as SEQ ID NO: 13, wherein the nucleotide sequence of the probe consists of the nucleotide sequence set forth as SEQ ID NO: 5;
   amplifying a *S. pneumoniae* nucleic acid by contacting the sample with a forward primer consisting of the nucleic acid sequence set forth as SEQ ID NO: 3 and a reverse primer consisting of the nucleic acid sequence set forth as SEQ ID NO: 4; and
   detecting hybridization between the *Streptococcus pneumoniae* nucleic acid and the probe, wherein the detection of hybridization indicates the presence of the *Streptococcus pneumoniae* nucleic acid in the sample.

2. The method according to claim 1, wherein the probe is labeled.

3. The method according to claim 2, wherein the probe is radiolabeled, fluorescently-labeled, biotin-labeled, enzymatically-labeled, or chemically-labeled.

4. The method according to claim 2, wherein the probe is labeled with a fluorophore, a fluorescence quencher, or a combination thereof.

5. The method according to claim 2, wherein detecting hybridization comprises detecting a change in signal from the labeled probe during or after hybridization relative to signal from the label before hybridization.

6. The method according to claim 1, wherein the method discriminates between *Streptococcus pneumoniae* nucleic acid and a pneumococcus-like viridans Streptococci (P-LVS) nucleic acid.

7. The method according to claim 1, wherein amplifying the *Streptococcus pneumoniae* nucleic acid comprises polymerase chain reaction (PCR), real-time PCR, reverse transcriptase-polymerase chain reaction (RT-PCR), real-time reverse transcriptase-polymerase chain reaction (rt RT-PCR), ligase chain reaction, or transcription-mediated amplification (TMA).

8. The method according to claim 1, wherein the sample is a biological sample obtained from a subject.

9. The method of claim 8, wherein the presence of a *Streptococcus pneumoniae* nucleic acid in the biological sample indicates the presence of a *Streptococcus pneumoniae* infection in the biological sample obtained from the subject.

10. The method according to claim 1, wherein the probe is arrayed in a predetermined array with an addressable location.

11. A method for diagnosing a *Streptococcus pneumoniae* infection in a subject suspected of having a *Streptococcus pneumoniae* infection comprising:

obtaining a sample comprising nucleic acids from the subject;

contacting the sample with one or more nucleic acid probes capable of hybridizing under very high stringency conditions to a *Streptococcus pneumoniae* nucleic acid sequence set forth as SEQ ID NO: 13, wherein the nucleotide sequence of the probe consists of the nucleotide sequence set forth as SEQ ID SEQ ID NO: 5;

amplifying a *S. pneumoniae* nucleic acid by contacting the sample with a forward primer consisting of the nucleic acid sequence set forth as SEQ ID NO: 3 and a reverse primer consisting of the nucleic acid sequence set forth as SEQ ID NO: 4; and detecting hybridization between a *Streptococcus pneumoniae* nucleic acid sequence present in the sample and the probe, wherein the detection of hybridization indicates that the subject is infected with *Streptococcus pneumoniae*.

12. The method according to claim 2, wherein the labeled probe comprises a fluorophore and a dark quencher or acceptor dye and the probe consists of X-GCCGAAAACGCT-TGATACAGGGAG-Y (SEQ ID NO: 5), wherein X is the fluorophore, and wherein Y is the dark quencher or acceptor dye.

13. The method according to claim 11, wherein the probe is labeled.

14. The method according to claim 13, wherein the labeled probe comprises a fluorophore and a dark quencher or acceptor dye and the probe consists of X-GCCGAAAACGCT-TGATACAGGGAG-Y (SEQ ID NO: 5), wherein X is the fluorophore, and wherein Y is the dark quencher or acceptor dye.

* * * * *

UNITED STATES PATENT AND TRADEMARK OFFICE
CERTIFICATE OF CORRECTION

PATENT NO. : 8,357,488 B2  
APPLICATION NO. : 12/600568  
DATED : January 22, 2013  
INVENTOR(S) : McGee et al.

Page 1 of 1

It is certified that error appears in the above-identified patent and that said Letters Patent is hereby corrected as shown below:

In the Specification:

Column 13, line 35, "(CO" should read --($C_t$)--.

Column 19, line 38, "32, 32" should read --32, 33--.

Column 33-34, Table 1, line 15, "5'-FAM TGCCGAAAACGCTTGATACAGGGAG-3'" should read --5'-FAM TGCCGAAAACGCTTGATACAGGGAG-3'--.

Column 33-34, Table 1, line 25, "*psaA-CDC* probea,b" should read --*psaA-CDC* probe $^{a,b}$--.

Column 33-34, Table 1, line 25, "5'-HEX CTAGCACATGCTACAAGAATGATTGC" should read --5'-HEX CTAGCACATGC$\underline{T}$ACAAGAATGATTGC--.

Column 33-34, Table 1, line 35, "*ply-CDC* probeb,c" should read --*ply-CDC* probe $^{b,c}$--.

Column 33-34, Table 1, line 36, "5'-FAM CTCAAGTTGGAAACCACGAGTAAGA" should read --5'-FAM CTCAAGT$\underline{T}$GGAAACCACGAGTAAGA--.

Column 33-34, Table 1, line 39, "$^{b,}$ T indicates" should read --$^{b,}$ $\underline{T}$ indicates--.

Column 33-34, Table 1, line 40, "CAL Flour 61" should read --CAL Fluor 610--.

Signed and Sealed this  
Twenty-ninth Day of July, 2014

Michelle K. Lee  
*Deputy Director of the United States Patent and Trademark Office*

SEQUENCE LISTING

<160> NUMBER OF SEQ ID NOS: 15

<210> SEQ ID NO 1
<211> LENGTH: 20
<212> TYPE: DNA
<213> ORGANISM: Artificial sequence
<220> FEATURE:
<223> OTHER INFORMATION: Hypothetical oligonulceotide.

```
<400> SEQUENCE: 1
atggtggacc cggtgggctt                                              20

<210> SEQ ID NO 2
<211> LENGTH: 20
<212> TYPE: DNA
<213> ORGANISM: Artificial sequence
<220> FEATURE:
<223> OTHER INFORMATION: Hypothetical oligonulceotide.

<400> SEQUENCE: 2
acgggggatc cggcgggcct                                              20

<210> SEQ ID NO 3
<211> LENGTH: 22
<212> TYPE: DNA
<213> ORGANISM: Artificial sequence
<220> FEATURE:
<223> OTHER INFORMATION: Synthetic oligonulceotide primer.

<400> SEQUENCE: 3
acgcaatcta gcagatgaag ca                                           22

<210> SEQ ID NO 4
<211> LENGTH: 21
<212> TYPE: DNA
<213> ORGANISM: Artificial sequence
<220> FEATURE:
<223> OTHER INFORMATION: Synthetic oligonulceotide primer.

<400> SEQUENCE: 4
tcgtgcgttt taattccagc t                                            21

<210> SEQ ID NO 5
<211> LENGTH: 24
<212> TYPE: DNA
<213> ORGANISM: Artificial sequence
<220> FEATURE:
<223> OTHER INFORMATION: Synthetic oligonulceotide probe.

<400> SEQUENCE: 5
gccgaaaacg cttgatacag ggag                                         24

<210> SEQ ID NO 6
<211> LENGTH: 25
<212> TYPE: DNA
<213> ORGANISM: Artificial sequence
<220> FEATURE:
<223> OTHER INFORMATION: Synthetic oligonulceotide probe.

<400> SEQUENCE: 6
tgccgaaaac gcttgataca gggag                                        25

<210> SEQ ID NO 7
<211> LENGTH: 27
<212> TYPE: DNA
<213> ORGANISM: Artificial sequence
<220> FEATURE:
<223> OTHER INFORMATION: Synthetic oligonulceotide primer.

<400> SEQUENCE: 7
gccctaataa attggaggat ctaatga                                      27
```

```
<210> SEQ ID NO 8
<211> LENGTH: 26
<212> TYPE: DNA
<213> ORGANISM: Artificial sequence
<220> FEATURE:
<223> OTHER INFORMATION: Synthetic oligonulceotide primer.

<400> SEQUENCE: 8
gaccagaagt tgtatctttt tttccg                                          26

<210> SEQ ID NO 9
<211> LENGTH: 35
<212> TYPE: DNA
<213> ORGANISM: Artificial sequence
<220> FEATURE:
<223> OTHER INFORMATION: Synthetic oligonulceotide probe.

<400> SEQUENCE: 9
ctagcacatg ctacaagaat gattgcagaa agaaa                                35

<210> SEQ ID NO 10
<211> LENGTH: 20
<212> TYPE: DNA
<213> ORGANISM: Artificial sequence
<220> FEATURE:
<223> OTHER INFORMATION: Synthetic oligonulceotide primer.

<400> SEQUENCE: 10
gcttatgggc gccaagtcta                                                 20

<210> SEQ ID NO 11
<211> LENGTH: 21
<212> TYPE: DNA
<213> ORGANISM: Artificial sequence
<220> FEATURE:
<223> OTHER INFORMATION: Synthetic oligonulceotide primer.

<400> SEQUENCE: 11
caaagcttca aaagcagcct c                                               21

<210> SEQ ID NO 12
<211> LENGTH: 33
<212> TYPE: DNA
<213> ORGANISM: Artificial sequence
<220> FEATURE:
<223> OTHER INFORMATION: Synthetic oligonulceotide probe.

<400> SEQUENCE: 12
ctcaagttgg aaaccacgag taagagtgat gaa                                  33

<210> SEQ ID NO 13
<211> LENGTH: 957
<212> TYPE: DNA
<213> ORGANISM: Streptococcus pneumoniae

<400> SEQUENCE: 13
ttattttact gtaatcaagc catctggctc tactgtgaat tctggcttgt ctgccagtgt     60
tccgtctggt ttgaggtagt accagcctgt tccgtccgct gactggataa aggcatttga    120
taccatggcg ccttctttag cgtctaagta gtaccaagtg tccttgtact tgacccagcc    180
tgtcttcatg gcaccttctt cgttgaaata gtaccactta tcagcgattt tcttccagcc    240
tgtagccatt tcgcctgagt tgtcgaacca gtaccagttg ccgtctgtgt gcttcctcca    300
gcggtctgca agcatatagc ctgaactgtc aaagtagtac caagtgccat tgattttctc    360
aaacttgtct tttggataag agccgtctga atgtacgtac cagtagccag tgtcattctt    420
```

```
ctgccagcct gtttcaatcg tcaagccgtt ctcaatatca tgcttaaact gctcacggct      480
aatgccccat ttagcaagat atggataagg gtcaacgtgg tctgagtggt tgtttggttg      540
gttattcgtg caatactcgt gcgttttaat tccagctaaa ctccctgtat caagcgtttt      600
cggcaaacct gcttcatctg ctagattgcg taagagttcg atataaaggc ggtagtccgt      660
catgaactct tctttggttg aatggctttc aatcagttca accgctgcat aggtctcagc      720
attccaaccg cccccaacgt cccaggcacc attatcaaca ggtcctacct gcatgatgca      780
accgttccca caatgtgcg agaaaaaacc taattctggg tctttccgcc agtgataatc      840
cgcttcattc tgtacggttg aatgcggatt cccagttgag tgtgcgtgta cttgcctata      900
tggttgcacg ccgacttgag gcaaatctgt tcttaattta ctcacattaa tttccat       957
```

<210> SEQ ID NO 14
<211> LENGTH: 1416
<212> TYPE: DNA
<213> ORGANISM: Streptococcus pneumoniae

<400> SEQUENCE: 14

```
ctagtcattt tctaccttat cctctacctg aggatagaga gttgttcccc aaatagaaat       60
cgtccgctta cgcactagtg gcaaatcggt tttttcataa accgtacgcc accattccca      120
ggcaagcccg gtacactctc taattttgac agagagatta cgaacattcc cttttaaagg      180
aatactagtg gtaaagtgag ccgtcaaatc ctgcccattt ctgtcccaag ccttaggagt      240
caagacttcc ttaccttgat gatcatagga taattcatcc caagtaatat aatattgggc      300
aacataggca ccactatgat ccagcagtaa atctccgttt ctgtaagctg taaccttagt      360
ctcaacatag tctgtactgt tttgaaaggt cgcaactaca ttgtcacgta aaaagaagt      420 tgtataggaa atcggcaagc ctggatgatc tgctgtaaag cgactgcctt cttgaatcaa      480
gtcctctacc atatccacct tgcctgttac aactcgggca cccgaacttg ggtcgccccc      540
taaaataacc gccttcactt ctgtattgtc caaaatctgc ttccactctg tctgaggagc      600
taccttgact cctttttatca agcttcaaa agcagcctct acttcatcac tcttactcgt      660
ggtttccaac ttgagataga cttggcgccc ataagcaaca ctcgaaatat agaccaaagg      720
acgctctgca gaaattcctc tctgttttaa atcctctacc gttacagtat cttgaaacac      780
atctcctgga ttttttaacag cgtctacgct gactgtataa taaatctgct taaaattaac      840
aatctgaatc tgcttttcac ctgaatggac agagttaaaa tcaatatcaa gagaattccc      900
tgtcttttca aagtcagaac caaacttgac cttgagttgt tccatgctgt gagccgttat      960
tttttcatac tgcattctag ctgggacatt attgacctga ccataatctt gatgccactt     1020
agccaacaaa tcgtttaccg ctccgcgaac acttgaattg ctggggtctt ccacttggag     1080
aaagctatcg ctacttgcca aaccaggcaa atcaatacta taagtcatcg gagcacgatc     1140
aaccgcaaga agagtgggat tattctctaa caaggtctca tccactacga gaagtgctcc     1200
aggatagagg cgactgtcgt tggtagctgt tacagaaata tcacttgtat ttgtcgacaa     1260
gctccgcttc tttctttcga taacaacaaa ctcatcgggt agctgattac cctctttgat     1320
gaaacgattt tcaatacttt ctccctgatg ggtcaagagt ttcttttat cgtaattcat     1380 agctagtata aagtcattta ctgctttatt tgccat                               1416
```

<210> SEQ ID NO 15
<211> LENGTH: 1330
<212> TYPE: DNA
<213> ORGANISM: Streptococcus pneumoniae

```
<400> SEQUENCE: 15
tactgcttca gttttgggac tctttattgg ctatagtttt aatgttgcgg caggttctag      60
tatcgtgctt acagctgcta gtttctttct cattagcttc tttatcgctc ccaaacaacg     120
atatttgaaa ctgaaaaata aacatttgtt aaaataaggg gcaaagccct aataaattgg     180
aggatctaat gaaaaaatta ggtacattac tcgttctctt tctttctgca atcattcttg     240
tagcatgtgc tagcggaaaa aaagatacaa cttctggtca aaaactaaaa gttgttgcta     300
caaactcaat catcgctgat attactaaaa atattgctgg tgacaaaatt gaccttcata     360
gtatcgttcc gattgggcaa gacccacacg aatacgaacc acttcctgaa gacgttaaga     420
aaacttctga ggctgatttg attttctata acggtatcaa ccttgaaaca ggtggcaatg     480
cttggtttac aaaattggta gaaaatgcca agaaaactga aaacaaagac tacttcgcag     540
tcagcgacgg cgttgatgtt atctaccttg aaggtcaaaa tgaaaaagga aaagaagacc     600
cacacgcttg gcttaacctt gaaaacggta ttattttgc taaaaatatc gccaaacaat     660
tgagcgccaa agaccctaac aataaagaat tctatgaaaa aaatctcaaa gaatatactg     720
ataagttaga caaacttgat aaagaaagta aggataaatt taataagatc cctgctgaaa     780
agaaactcat tgtaaccagc gaaggagcat tcaaatactt ctctaaagcc tatggtgtcc     840
caagtgccta catctgggaa atcaatactg aagaagaagg aactcctgaa caaatcaaga     900
ccttggttga aaaacttcgc caaacaaaag ttccatcact ctttgtagaa tcaagtgtgg     960
atgaccgtcc aatgaaaact gtttctcaag acacaaacat cccaatctac gcacaaatct    1020
ttactgactc tatcgcagaa caaggtaaag aaggcgacag ctactacagc atgatgaaat    1080
acaaccttga caagattgct gaaggattgg caaaataagc ctctgaaaaa cgtcattctc    1140
atgtgagctg gcgttttttc tatgcccaca tttccggtca aatcattgga aaattctgac    1200
tgtttcagat acaatggaag aaaaaagatt ggagtatcct atggtaactt ttctcggaaa    1260
tcctgtgagc tttacaggta aacaactaca agtcggcgac aaggcgcttg attttctct    1320 tactacaaca                                                          1330
```